United States Patent
Nelson et al.

(10) Patent No.: US 9,400,270 B2
(45) Date of Patent: *Jul. 26, 2016

(54) TESTING WATER CONTAMINATION IN GEOGRAPHIC AREAS

(71) Applicant: FracTest LLC, Dallas, TX (US)

(72) Inventors: Scott Nelson, Dallas, TX (US); Sa'd Shannak, Dallas, TX (US)

(73) Assignee: FracTest LLC, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/572,154

(22) Filed: Dec. 16, 2014

(65) Prior Publication Data

US 2015/0241403 A1 Aug. 27, 2015

Related U.S. Application Data

(63) Continuation of application No. 14/248,550, filed on Apr. 9, 2014, now Pat. No. 8,918,285.

(60) Provisional application No. 61/944,429, filed on Feb. 25, 2014.

(51) Int. Cl.
*G01N 33/18* (2006.01)
*G06F 17/30* (2006.01)
*G06Q 10/06* (2012.01)

(52) U.S. Cl.
CPC .......... *G01N 33/18* (2013.01); *G06F 17/30241* (2013.01); *G06Q 10/067* (2013.01)

(58) Field of Classification Search
CPC ... G01N 33/18; G06F 17/30; G06F 17/30241; G06Q 10/06; G06Q 10/0635; G06Q 10/0639; G06Q 10/06395
See application file for complete search history.

(56) References Cited

U.S. PATENT DOCUMENTS 8,918,285 B1 * 12/2014 Nelson ................... G01N 33/18
702/2

OTHER PUBLICATIONS

Mitchell W. Winiecki, Application of the Advection-Dispersion Equation in GIS to Analyze the Risks to Groundwater Resources as a Result of Hydraulic Fracturing, 2012, Resources Analysis, vol. 14, Saint Mary's University of Minnesota Central Service Press, Winona, MN, 12 pp.*

* cited by examiner

*Primary Examiner* — Toan Le
(74) *Attorney, Agent, or Firm* — Fish & Richardson P.C.

(57) ABSTRACT

One example of testing for water contamination in geographic areas to determine a risk of water contamination includes determining a risk of water contamination. A computer system receives identification of a geographic area in which a risk of water contamination is to be determined. In response, the system determines a number of potential complaints of water contamination in the geographic area by applying the number of one or more correlated sources of water contamination located in the geographic area. The system determines a risk factor representing a risk of water contamination in the geographic area based, in part, on the number of potential complaints. The system can provide the risk factor as the risk of water contamination in the geographic area.

19 Claims, 17 Drawing Sheets

TESTING WATER CONTAMINATION IN GEOGRAPHIC AREAS

TECHNICAL FIELD

This disclosure relates to testing for contamination of fluids and environmental impairment, such as water, from sources built by human activity.

BACKGROUND

Underground water sources face the risk of contamination from various sources of human activity, e.g., landfills, coal mines, wells, fracture treatments, and other sources. Bodies that govern geographic areas (e.g., municipalities, counties, states, countries, or other geographic areas) often receive requests to perform operations in the areas. For example, the governing bodies receive requests to form wells or coal mines, or to lay underground pipelines to transport fluids (e.g., liquids, gases, or other fluids), some of which can be hazardous. The governing bodies have an interest in determining a risk that such operations will contaminate the water in the geographic area which is likely being daily used by residents of the area.

SUMMARY

This disclosure relates to computer-implemented methods, computer-readable storage media, and computer systems for testing water contamination in geographic areas.

Certain implementations of the subject matter described here can be implemented as a computer-implemented method to determine a risk of water contamination. A computer system receives identification of a geographic area in which a risk of water contamination is to be determined. In response to receiving the identification of the geographic area, the computer system identifies multiple sources of water contamination located in the geographic area. The computer system determines a subset of the multiple sources that have a greater likelihood of causing water contamination in the geographic area compared to sources that are not included in the subset. The computer system identifies multiple variables associated with the subset of the multiple sources. The multiple variables include a number of each source of water contamination included in the subset. The computer system identifies a model to determine a number of potential complaints of water contamination in the geographic area. The model is based, in part, on the number of each source of water contamination and environmental impairment in the subset. The computer system determines a number of potential complaints of water contamination in the geographic area by applying the number of each source of water contamination located in the subset to the model. The computer system determines a risk factor representing a risk of environmental impairment, e.g., water contamination, or other environmental impairment, in the geographic area based, in part, on the number of potential complaints. The computer system can provide the risk factor as the risk of water contamination in the geographic area.

This, and other aspects, can include one or more of the following features. Determining the subset of the multiple sources can include performing a correlation analysis on the multiple sources located in the geographic area, and identifying correlated sources to include in the subset. Identifying the multiple variables can include accessing multiple databases that store information associated with the multiple sources located in the geographic area. The information can include the multiple variables. The computer system can retrieve the multiple variables from one or more of the multiple databases. The multiple sources of water contaminations can include multiple anthropogenic sources including at least one or more of a landfill, a coal mine, a reported accident hazard liquid, a reported incident gas distribution, or incident gas transmission gathering. The model can be represented by $Y = 3.21 - (0.04 \cdot A) + (0.79 \cdot B) + (0.16 \cdot C) + (0.15 \cdot D) + (0.01 \cdot E)$. Y can represent represents the number of potential complaints of water contamination, and A, B, C, D and E can represent a number of landfills, a number of coal mines, a number of reported accident hazard liquid, a number of incident gas distribution, and a number of incident gas transmission gathering, respectively. The model can represent the risk of environmental impairment in U.S.A. The multiple sources of water contaminations can include multiple wells including at least one or more of plugged wells, active wells, injection wells, or orphaned wells. The model can be represented by $Y = 43.7 + (6.11 \cdot P) + (0.018 \cdot A) - (1.78 \cdot O)$. Y can represent the number of potential complaints of water contamination, and P, A, and O can represent a number of plugged wells, a number of active wells, and a number of orphaned wells, respectively. Determining a risk factor representing a risk of water contamination in the geographic area based, in part, on the number of potential complaints can include determining that the number of potential complaints is greater than a first threshold number of potential complaints, and determining that the geographic area has a high risk factor for water contamination in response to determining that the number of potential complaints is greater than a first threshold number of potential complaints. Determining a risk factor representing a risk of water contamination in the geographic area based, in part, on the number of potential complaints can include determining that the number of potential complaints is less than or equal to the first threshold and greater than a second threshold that is less than the first threshold, and determining that the geographic area has a medium risk factor for water contamination in response to determining that the number of potential complaints is less than or equal to the first threshold and greater than the second threshold. Determining a risk factor representing a risk of water contamination in the geographic area based, in part, on the number of potential complaints can include determining that the number of potential complaints is less than or equal to the second threshold, and determining that the geographic area has a low risk factor for water contamination in response to determining that the number of potential complaints is less than or equal to the second threshold. The first threshold can be 110 and the second threshold can be 55. The computer system can develop the model to determine a number of potential complaints of water contamination in the geographic area by performing statistical operations on the plurality of variables to determine the number of potential complaints and determining a coefficient for each source of water contamination based, in part, on results of the statistical operations. The statistical operations can include at least one of a multiple regression analysis or an analysis of variance. The computer system can build correlations between the multiple variables by performing statistical tests including at least one of a normality test, a linearity test, a reliability of measurement test, or a homoscedasticity test to ensure the validity of the developed model.

Certain aspects of the subject matter described here can be implemented as a computer-readable medium storing instructions executable by data processing apparatus to perform the operations described here. Certain aspects of the subject matter described here can be implemented as a computer system that includes data processing apparatus and a computer-readable medium storing instructions executable by data processing apparatus to perform the operations described here.

While generally described as computer-implemented software embodied on tangible media that processes and transforms the respective data, some or all of the aspects may be computer-implemented methods or further included in respective systems or other devices for performing this described functionality. The details of these and other aspects and implementations of the present disclosure are set forth in the accompanying drawings and the description below. Other features and advantages of the disclosure will be apparent from the description and drawings, and from the claims.

DESCRIPTION OF DRAWINGS

Like reference symbols in the various drawings indicate like elements.

DETAILED DESCRIPTION

This disclosure relates to computer-implemented methods, computer-readable storage media, and computer systems for testing water contamination in geographic areas. Example implementations of the subject matter as described below in the context of testing water contamination in geographic areas at varying levels of granularity (e.g., municipalities, counties that include municipalities, states that include counties, countries that include states, or other levels of granularity). The subject matter can, alternatively or in addition, be implemented to test any type of environmental impairment in geographic areas (e.g., agricultural fields, wild life, or other geographic areas) due to any potential source of contamination (e.g., landfills, coal mines, hydraulic fracking, wells, or other potential sources).

Figure 1:
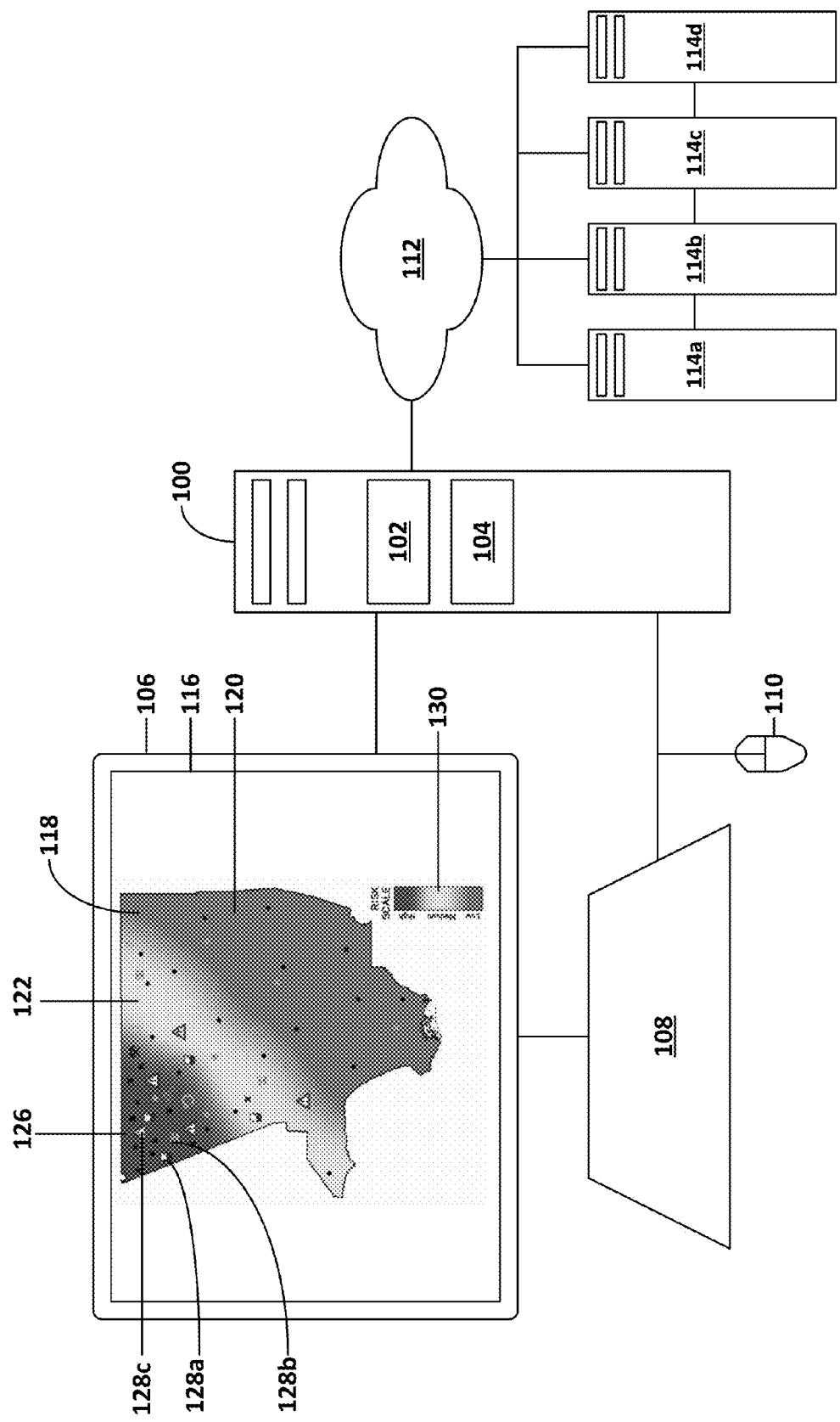
FIG. 1 is a schematic diagram of an example of a computer system for presenting risks of water contamination in multiple geographic areas.

FIG. 1 is a schematic diagram of an example of a computer system 100 for presenting risks of water contamination in multiple geographic areas. The computer system 100 can include a computer-readable medium 102 storing computer instructions executable by data processing apparatus 104 (e.g., one or more processors) to perform operations. The computer system 100 can be connected to a display device 106 (e.g., a cathode ray tube monitor, a liquid crystal display monitor, or other display devices) and to one or more input devices (e.g., a keyboard 108, a mouse 110, or other input devices). In some implementations, the computer system 100 can be connected to multiple server computer systems (e.g., a first server computer system 114a, a second server computer system 114b, a third server computer system 114c, a fourth server computer system 114d, and/or other server computer systems). Each server computer system can include a respective computer-readable medium (e.g., a database) to store information and data processing apparatus to execute computer instructions to perform operations. For example, each server computer system can host a website and store resources executable to present the website on one or more respective databases. As described below, the computer system 100 can retrieve information associated with one or more sources of water contamination by accessing the respective databases of one or more of the server computer systems.

In some implementations, the computer system 100 can develop a mathematical model to determine a number of effective claims from sources of water contamination in a geographic area. An effective claim is an estimate of a future general claim of water contamination to be established as a confirmed claim in the geographic area. For example, the computer system 100 can input a number of sources of water contamination in the state of Texas. The computer system 100 can input the number of sources, among other inputs, to the model to determine that, out of several claims of water contamination that can be filed in the geographic area in the future, 70 claims are likely to be confirmed claims. In other words, the computer system 100 can determine that the number of effective claims from the sources of water contamination to be 70. In this manner, the computer system 100 can develop a correlation between general claims and confirmed claims to predict future confirmed claims in a specific geographic area.

As described below, the computer system 100 can develop a mathematical model for each source of water contamination in the geographic area. In some implementations, the computer system 100 can develop the model by correlating general claims reported by various sources, e.g., environmental agencies or other sources, on a national level, and confirmed claims in which causality has been established between potential sources of contamination (e.g., hydraulic fracking, landfills, coal mines, or other potential sources) and contamination based on governmental reports. The computer system 100 can filter and define the general claims to include environmental and health safety causes. The computer system 100 can obtain the data on a county level and aggregate the data to represent each state for 50 states in the U.S.A.

Figure 2:
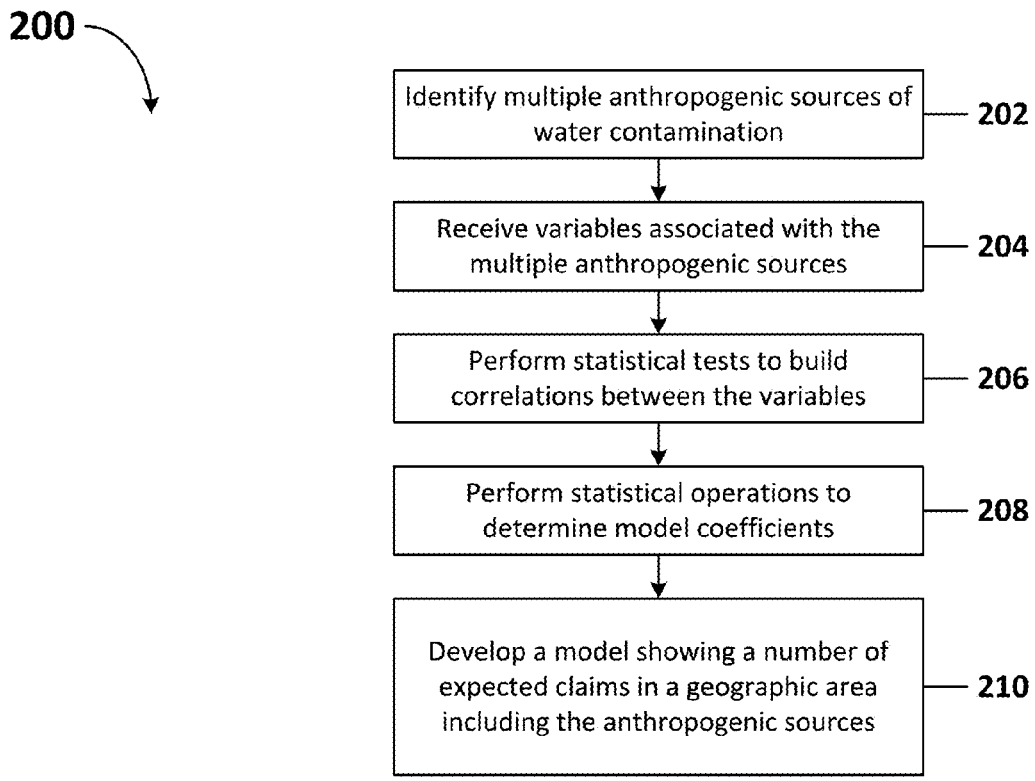
FIG. 2 is a flowchart of an example of a process to develop a mathematical model to determine a number of effective claims of water contamination in a geographic area from anthropogenic sources.

FIG. 2 is a flowchart of an example of a process 200 to develop a mathematical model to determine a number of effective claims of water contamination in a geographic area from anthropogenic sources. Anthropogenic sources are sources of environmental contamination originating in human activity in the geographic area. Examples of anthropogenic sources can include at least one or more of a landfill, a coal mine, a reported accident hazard liquid, a reported incident gas distribution, or an incident gas transmission gathering. The process 200 can be implemented as computer instructions stored on the computer-readable medium 102 and executed by the data processing apparatus 104.

At 202, multiple anthropogenic sources of water contamination in a geographic area can be identified. For example, the computer system 100 can receive an identification of a geographic area. The identification can include, e.g., latitude and longitude coordinates associated with the geographic area, the name of the area, an address, or other type of identification. The geographic area can be divided hierarchically and identified at each level in the hierarchy. For example, the root node of the hierarchy can be a country (e.g., U.S.A.), and each leaf node in the hierarchy can identify a municipality. Intermediate nodes in the hierarchy can identify, e.g., a state, a county, or additional granular geographic levels.

Multiple anthropogenic sources of water contamination can be present in an identified geographic area. For example, the leaf node in the hierarchy, which represents the most granular geographic level, can include one or more coal mines, one or more landfills, one or more locations at which gas distribution was reported, or other anthropogenic sources. In response to receiving the identification of the most granular level of the geographic area, the computer system 100 can identify the anthropogenic sources in the area.

In some situations, the geographic area is at a level in the hierarchy that is above the leaf node. In such situations, the computer system 100 can identify the level of the geographic area in the hierarchy and further identify children nodes for the level. The computer system 100 can identify the anthropogenic sources in the area by aggregating the anthropogenic sources at each child node. For example, the identified geographic area can be a county that includes multiple municipalities. The computer system 100 can identify each municipality in the county, and further identify the anthropogenic sources in each of the identified municipalities. In this manner, the computer system 100 can identify the anthropogenic sources in the country by aggregating the anthropogenic sources in each identified municipality. In another example in which the identified geographic area is a state, the computer system 100 can identify the anthropogenic sources by aggregating the anthropogenic sources in each county in the state.

At 204, variables associated with the multiple anthropogenic sources are received. The variables can include one or more of a number of anthropogenic sources in the geographic area, or a location and/or a distance of each anthropogenic source from a reference location in the geographic area, combinations of them or other variables.

For example, the computer system 100 can access the Department of Energy's server computer system that includes a database that stores total numbers of coal mines in a geographic area and a location of each coal mine in the area. To do so, the computer system 100 can transmit a search query requesting the number and locations of the coal mines in the geographic area to the Department of Energy's server computer system. The computer system 100 can receive the number and the locations in response to the search query. In another example, the computer system 100 can access the U.S. Environmental Protection Agency's server computer system that includes a database storing landfills data, e.g., under landfill gas energy projects and candidate landfills. The computer system 100 can receive the number and locations of the landfills in response to providing a search query to the server computer system. In a further example, the computer system 100 can receive linear pipeline data and incidents from a server computer system of the Department of Transportation's pipeline and hazardous materials safety administration. Confirmed claims of water contamination are reported on a county level. The computer system 100 can receive the confirmed claims from one or more server systems that host such confirmed claims.

At 206, statistical tests can be performed to build correlations between the variables. For example, the computer system 100 can perform a correlation analysis on the multiple sources located in the geographic area to identify correlated sources. For further analysis, the computer system 100 can use only the sources included in the subset. In some implementations, the computer system 100 can filter the multiple sources to include water contamination complaints due to environmental and health safety causes. Alternatively or in addition, the computer system 100 can filter the multiple sources to identify water contamination complaints that were determined to have been caused by performing fracture treatments.

Figure 5A:
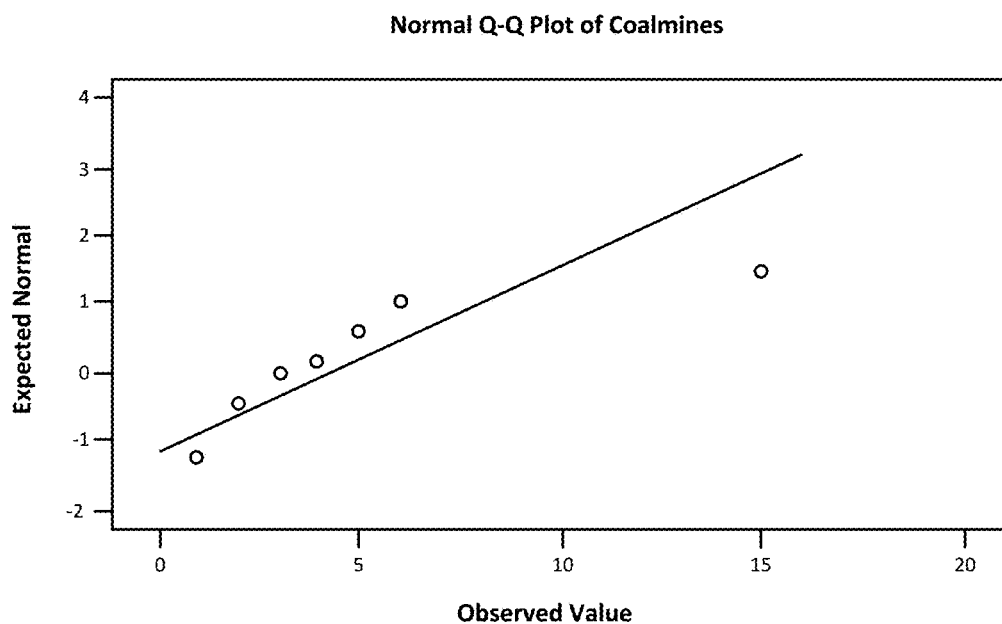
FIGS. 5A-5E are plots showing normality tests performed for multiple sources of water contamination.
Figure 5B:
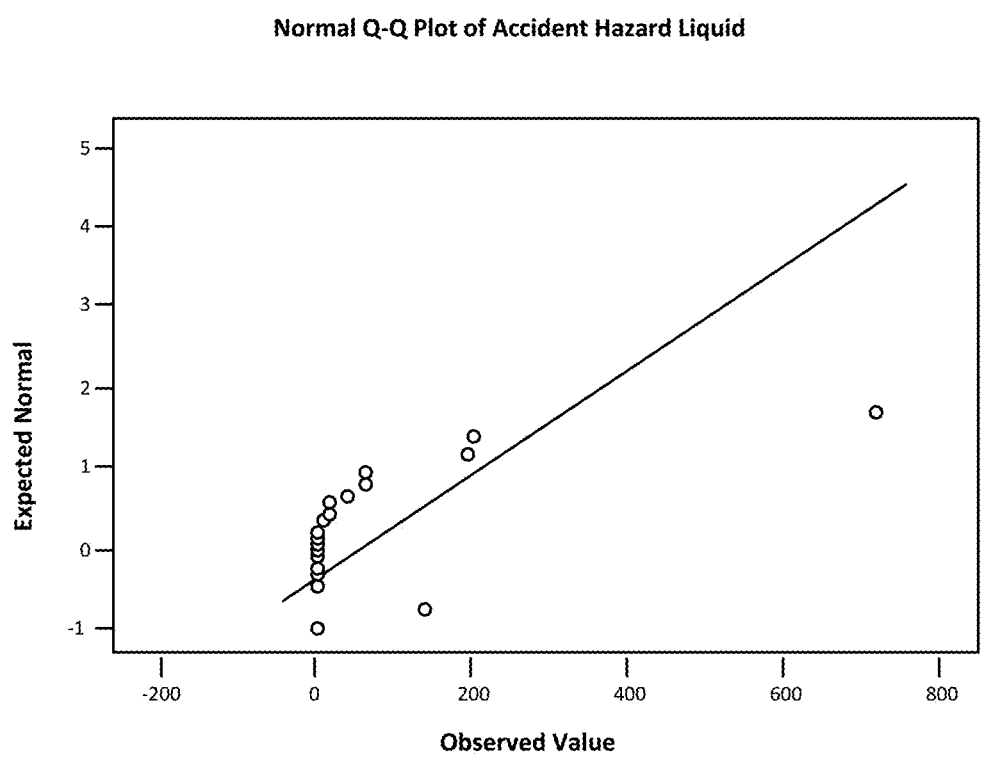
Figure 5C:
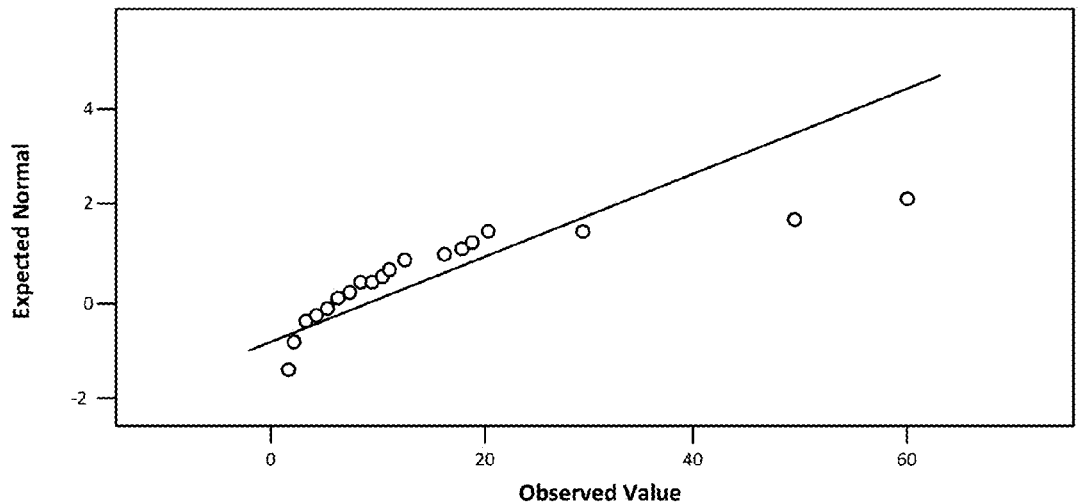
Figure 5D:
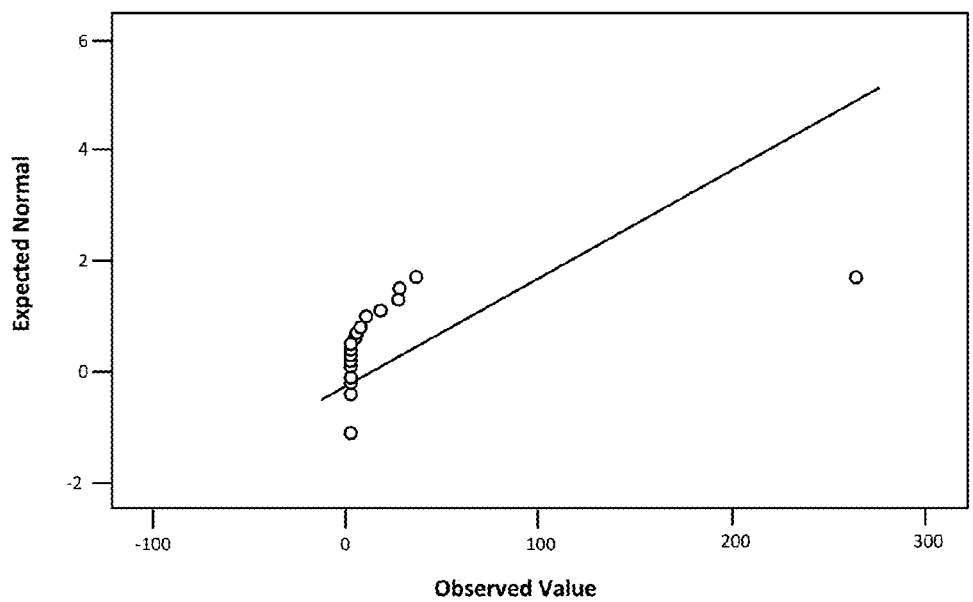
Figure 5E:
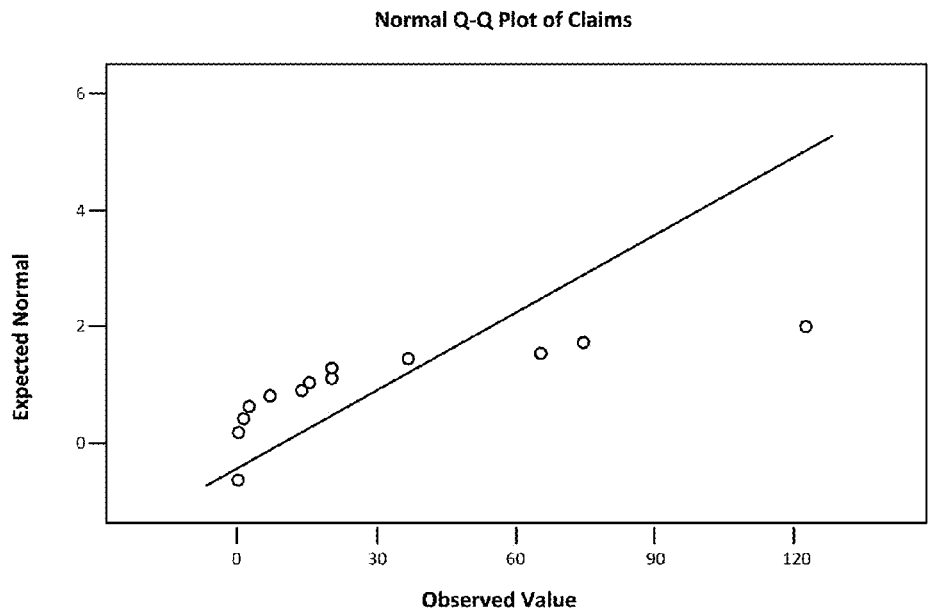

In some implementations, the computer system 100 can determine correlations between the multiple variables by implementing statistical tests including one or more of a normality test, a linearity test, a reliability of the measurement test, a homoscedasticity test, or other tests, for each source of water contamination in the subset. FIG. 5A is a plot showing an output (e.g., a Normal Q-Q plot) of a normality test implemented by the computer system 100 for coal mines in the geographic area. FIG. 5B is a plot showing an output of a normality test implemented by the computer system 100 for accident hazard liquid in the geographic area. FIG. 5C is a plot showing an output of a normality test implemented by the computer system 100 for incident gas distribution in the geographic area. FIG. 5D is a plot showing an output of a normality test implemented by the computer system 100 for incident gas transmission gathering in the geographic area. FIG. 5E is a plot showing an output of a normality test implemented by the computer system 100 for confirmed claims in the geographic area. The computer system 100 can implement the normality test to ensure that data collected are normally distributed, and exclude skewed or kurtotic variables or variables with substantial outliers, which can distort relationships and significance tests. The computer system 100 can implement normality tests for all the variables associated with each anthropogenic source in the subset to generate plots such as those shown in FIGS. 5A-5E.

Table 1 shows an outcome of normality tests implemented at 95% confidence for landfills.

TABLE 1

Landfills—Normality Test at 95% confidence
Tests of Normality

| | Kolmogorov-Smirnov[a] | | | Shapiro-Wilk | | |
|---|---|---|---|---|---|---|
| | Statistic | df | Sig. | Statistic | df | Sig. |
| Landfills | .232 | 50 | .000 | .748 | 50 | .000 |

[a]Lilliefors Significance Correction

Since the p-value in the Shapiro-Wilk test is less than 0.05, there is a significance level between and among means at 95% confidence.

Table 2 shows an outcome of normality tests implemented at 95% confidence for coal mines.

TABLE 2

Coal mines—Normality Test at 95% confidence
Tests of Normality

| | Kolmogorov-Smirnov[a] | | | Shapiro-Wilk | | |
|---|---|---|---|---|---|---|
| | Statistic | df | Sig. | Statistic | df | Sig. |
| Coalmines | .247 | 13 | .029 | .721 | 13 | .001 |

[a]Lilliefors Significance Correction

Since the p-value in the Shapiro-Wilk test is less than 0.05, there is a significance level between and among means at 95% confidence.

Table 3 shows an outcome of normality tests implemented at 95% confidence for accident hazard liquid.

TABLE 3

Accident hazard liquid—Normality Test at 95% confidence
Tests of Normality

| | Kolmogorov-Smirnov[a] | | | Shapiro-Wilk | | |
|---|---|---|---|---|---|---|
| | Statistic | df | Sig. | Statistic | df | Sig. |
| Accident Hazard Liquid | .347 | 23 | .000 | .438 | 23 | .000 |

[a]Lilliefors Significance Correction

Since the p-value in the Shapiro-Wilk test is less than 0.05, there is a significance level between and among means at 95% confidence.

Table 4 shows an outcome of normality tests implemented at 95% confidence for incident gas distribution.

TABLE 4

Incident Gas Distribution—Normality Test at 95% confidence

| | Kolmogorov-Smirnov[a] | | | Shapiro-Wilk | | |
|---|---|---|---|---|---|---|
| | Statistic | df | Sig. | Statistic | df | Sig. |
| Incident Gas Distribution | .237 | 47 | .000 | .664 | 47 | .000 |

[a]Lilliefors Significance Correction

Since the p-value in the Shapiro-Wilk test is less than 0.05, there is a significance level between and among means at 95% confidence.

Table 5 shows an outcome of normality tests implemented at 95% confidence for incident gas transmission gathering.

TABLE 5

Incident Gas Transmission Gathering—Normality Test at 95% confidence
Tests of Normality

| | Kolmogorov-Smirnov[a] | | | Shapiro-Wilk | | |
|---|---|---|---|---|---|---|
| | Statistic | df | Sig. | Statistic | df | Sig. |
| incident gas transmission gathering | .377 | 26 | .000 | .306 | 26 | .000 |
| incident gas transmission gathering | .377 | 26 | .000 | .306 | 26 | .000 |

[a]Lilliefors Significance Correction

Since the p-value in the Shapiro-Wilk test is less than 0.05, there is a significance level between and among means at 95% confidence.

Table 6 shows an outcome of normality tests implemented at 95% confidence for confirmed claims.

TABLE 6

Tests of Normality
Confirmed Claims—Normality Test at 95% confidence

| | Kolmogorov-Smirnov[a] | | |
|---|---|---|---|
| | Statistic | df | Sig. |
| Confirmed claims | .260 | 2 | .000 |

[a]Lilliefors Significance Correction

Since the p-value in the Shapiro-Wilk test is less than 0.05, there is a significance level between and among means at 95% confidence.

Table 7 shows an outcome of normality tests implemented at 95% confidence for claims.

TABLE 7

Claims—Normality Tests at 95% confidence
Tests of Normality

| | Kolmogorov-Smirnov[a] | | | Shapiro-Wilk | | |
|---|---|---|---|---|---|---|
| | Statistic | df | Sig. | Statistic | df | Sig. |
| Claims | .378 | 50 | .000 | .437 | 50 | .000 |

[a]Lilliefors Significance Correction

Since the p-value in the Shapiro-Wilk test is less than 0.05, there is a significance level between and among means at 95% confidence.

Figure 6A:
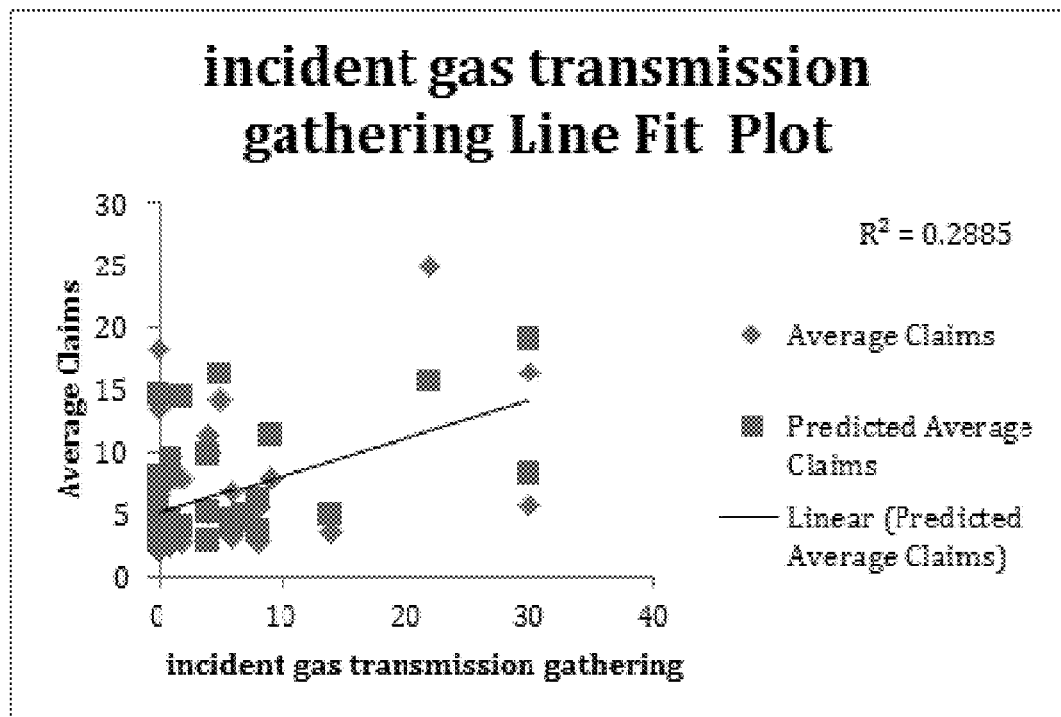
FIGS. 6A-6H are plots showing linearity tests performed for multiple sources of water contamination.
Figure 6B:
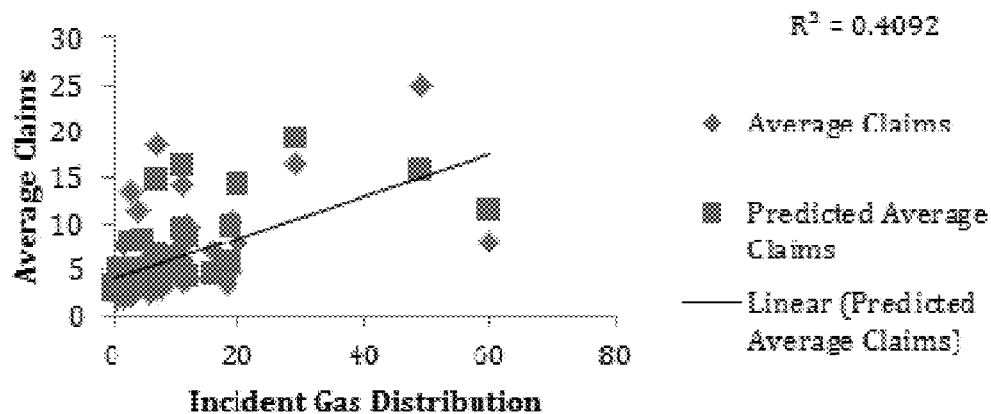
Figure 6C:
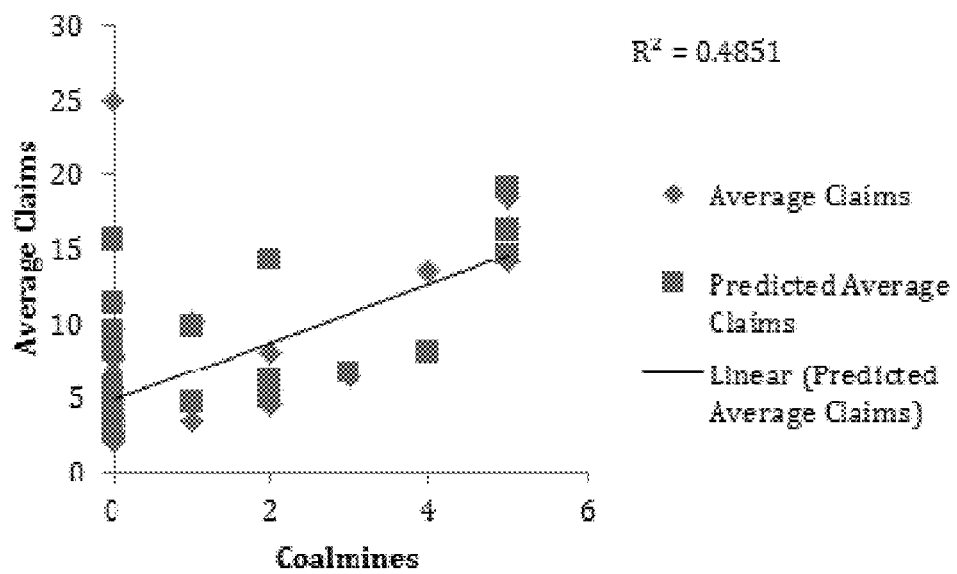
Figure 6D:
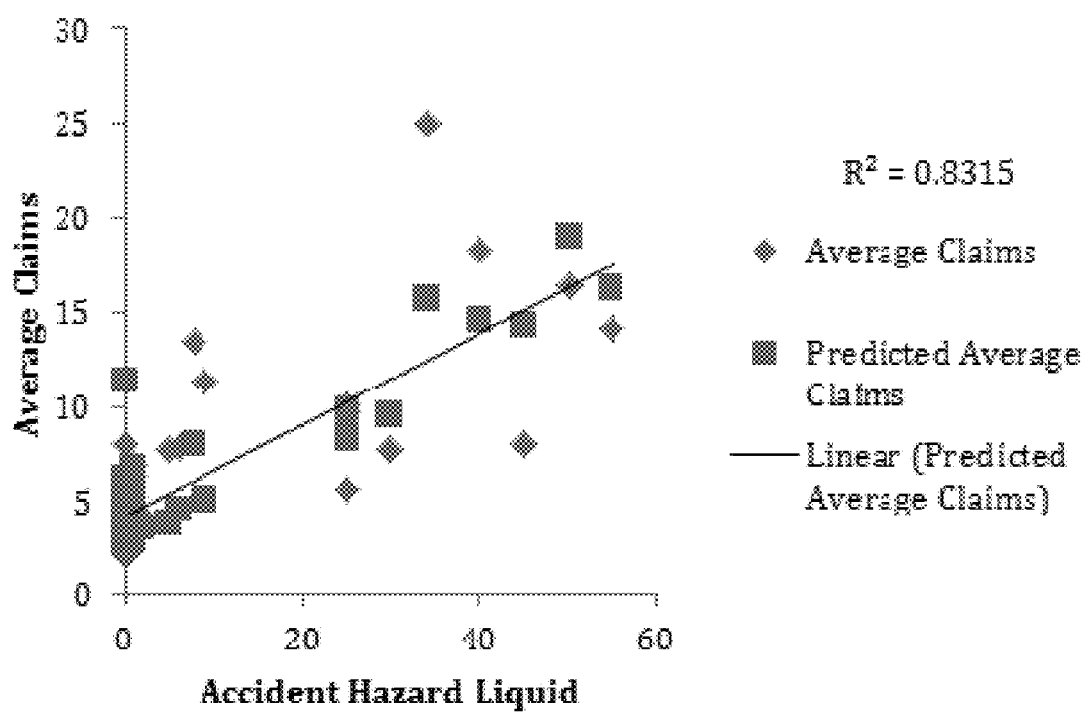
Figure 6E:
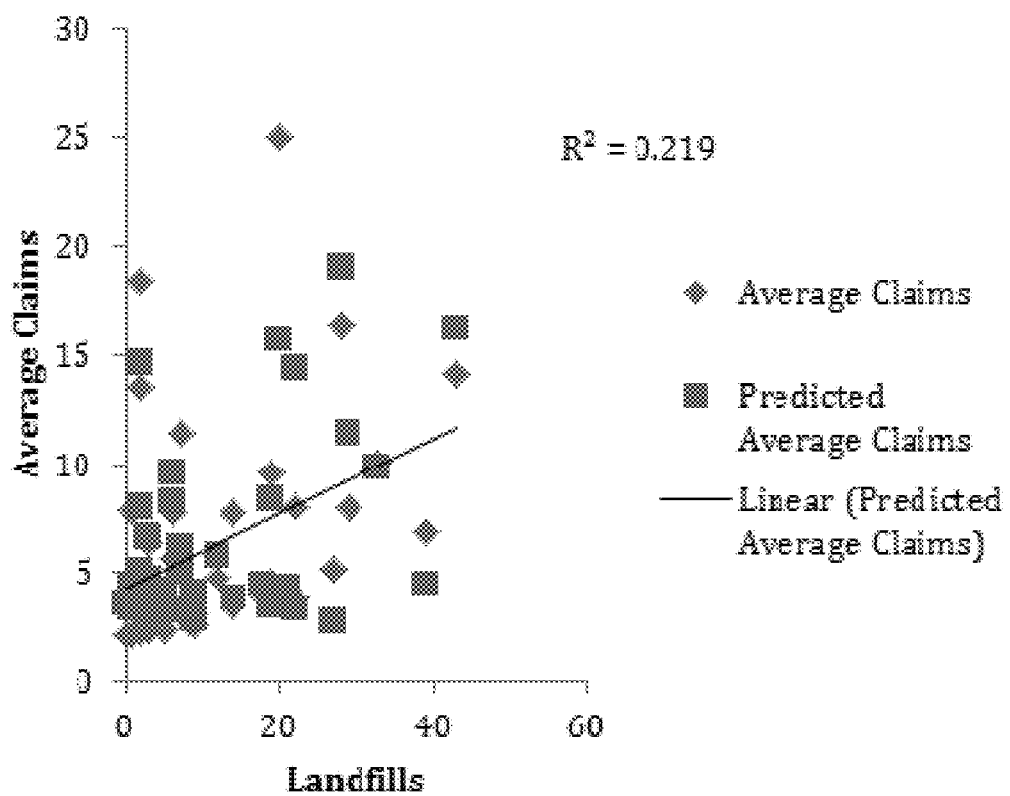

FIG. 6A is a plot showing an output (e.g., a Line Fit plot) of a linearity test implemented by the computer system 100 for incident gas transmission. FIG. 6B is a plot showing an output of a linearity test implemented by the computer system 100 for the incident gas distribution line. FIG. 6C is a plot showing an output of a linearity test implemented by the computer system 100 for coal mines. FIG. 6D is a plot showing an output of a linearity test implemented by the computer system 100 for accident hazard liquid. FIG. 6E is a plot showing an output of a linearity test implemented by the computer system 100 for landfills. Each of the sources represented in FIGS. 6A-6E are included in the geographic area. The computer system 100 can implement the linearity tests to avoid "Type II" errors or to avoid under-estimating the true relationship between the variables associated with the anthropogenic sources in the subset.

The computer system 100 can implement reliability of the measurement tests to ensure that all variables are measured without error, e.g., measurement error, Type II error, or other errors. The computer system 100 can implement the homoscedasticity test to ensure that the variance of errors is the same across all levels of independent variables, i.e., there is homogeneity of variance.

At 208, statistical operations can be performed to determine coefficients for the mathematical model. For example, after confirming the validity of the analysis and getting positive results from the tests described above, the computer system 100 can be implemented to study the relationships among the variables. In some implementations, the computer system 100 can be implemented to execute statistical computer software to study the relationships among the variables. For example, the computer system 100 can implement a multiple regression analysis to arrive at the mathematical model that can predict a number of potential complaints of water contamination in the geographic area (e.g., the effective claims).

An example of interaction and correlations between variables is shown in Tables 8 and 9.

TABLE 8

Inter-Item Correlation Matrix

| | Accident Hazard Liquid | Incident Gas Distribution | incident gas transmission gathering |
|---|---|---|---|
| Accident Hazard Liquid | 1.000 | .258 | .947 |
| Incident Gas Distribution | .258 | 1.000 | .374 |
| incident gas transmission gathering | .947 | .374 | 1.000 |

TABLE 9

Inter-Item Covariance Matrix

| | Accident Hazard Liquid | Incident Gas Distribution | incident gas transmission gathering |
|---|---|---|---|
| Accident Hazard Liquid | 38632.103 | 658.103 | 13273.564 |
| Incident Gas Distribution | 658.103 | 168.936 | 346.564 |
| incident gas transmission gathering | 13273.564 | 346.564 | 5087.103 |

Table 10 is an example of item-total statistics. All coefficients are positive indicating positive correlation between variables.

TABLE 10

Item-Total Statistics

| | Scale Mean if Item Deleted | Scale Variance if Item Deleted | Corrected Item-Total Correlation | Squared Multiple Correlation | Cronbach's Alpha if Item Deleted |
|---|---|---|---|---|---|
| Accident Hazard Liquid | 41.00 | 5949.167 | .919 | .907 | .233 |
| Incident Gas Distribution | 131.00 | 70266.333 | .292 | .229 | .756 |
| incident gas transmission gathering | 119.08 | 40117.244 | .953 | .915 | .066 |

An example of regression statistics generated by the computer system 100 for anthropogenic sources is shown below.

TABLE 11

Regression Statistics

| Multiple R | 0.836425 |
|---|---|
| R Square | 0.699607 |
| Adjusted R Square | 0.659013 |
| Standard Error | 2.894409 |
| Observations | 50 |

Table 11 shows that Cronbach's Alpha value was positive indicating that 52% of the score is considered reliable, and that all the variables have the same variance (71%), which is considered a reliable score.

The regression statistics table (Table 11) provides useful descriptive statistics, including the multiple R (R is the square root of R-Squared and is the correlation between the observed and predicted values of dependent variable), $R^2$ (this is the proportion of variance in the dependent variable which can be explained by the independent variables), Adjusted R-square (this is an adjustment of the R-squared that penalizes the addition of extraneous predictors to the model), Standard Error of the estimate (this is also referred to as the root mean squared error, and finally total number of observations).

From the previous regression statistics table, 70% of variance in the dependent variable (i.e., the effective claims) can be explained by the independent variables. This percentage is considered a high for such field of study and the reliability of the developed model is also high. To further assess the significance of the developed model, the computer system 100 implemented an analysis of variance (ANOVA), generated Table 12 (below), and determined the p-value. The output of the ANOVA analysis shows whether we have a statistically significant difference between our group means. The p-value is lower than 0.05 which implies that the test is statistically significant and 95% of the time properly constructed confidence intervals should contain the true value of the variable of interest (EC).

TABLE 12

ANOVA analysis

ANOVA

| | df | SS | MS | F | Significance F |
|---|---|---|---|---|---|
| Regression | 5 | 721.9151 | 144.383 | 17.2344 | 0.00 |
| Residual | 44 | 309.9714 | 8.377606 | | |
| Total | 49 | 1031.887 | | | |

At 210, a model showing a number of expected claims in a geographic area including the anthropogenic sources is developed. The computer system 100 can develop the mathematical model based on coefficients outputs from the ANOVA table shown in Table 13. As Table 13 shows, all coefficients are significant at 95% confidence level except for two variables landfills and incident gas transmission gathering.

TABLE 13

ANOVA table

| | Coefficients | Standard Error | t Stat | P-value | Lower 95% | Upper 95% | Lower 90.0% | Upper 90.0% |
|---|---|---|---|---|---|---|---|---|
| Intercept | 3.21 | 0.67 | 4.80 | 0.00 | 1.86 | 4.56 | 2.08 | 4.34 |
| Landfills | −0.04 | 0.05 | −0.71 | 0.48 | −0.14 | 0.07 | −0.12 | 0.05 |
| Coalmines | 0.79 | 0.40 | 1.99 | 0.05 | −0.02 | 1.59 | 0.12 | 1.46 |

TABLE 13-continued

ANOVA table

|  | Coefficients | Standard Error | t Stat | P-value | Lower 95% | Upper 95% | Lower 90.0% | Upper 90.0% |
|---|---|---|---|---|---|---|---|---|
| Hazard Liquid Accident | 0.16 | 0.04 | 3.65 | 0.00 | 0.07 | 0.25 | 0.09 | 0.24 |
| Incident Gas Distribution | 0.15 | 0.05 | 3.12 | 0.00 | 0.05 | 0.25 | 0.07 | 0.23 |
| incident gas transmission gathering | 0.01 | 0.07 | 0.20 | 0.84 | −0.14 | 0.17 | −0.11 | 0.14 |

The model developed by the computer system 100 for anthropogenic sources can be represented by Equation 1.

$$Y = 3.21 - 0.04A + 0.79B + 0.16C + 0.15D + 0.01E \quad \text{(Equation 1)}$$

In Equation 1, Y represents the number of potential complaints of water contamination, and A, B, C, D and E represent a number of landfills, a number of coal mines, a number of reported accident hazard liquid, a number of incident gas distribution, and a number of incident gas transmission gathering, respectively. The computer system 100 determined the mathematical model shown in Equation 1 for a geographic area based, in part, on the anthropogenic sources included in the area. The computer system 100 can implement similar techniques to determine respective mathematical models for different geographic areas based, in part, on the anthropogenic sources included in those areas.

In some implementations, the computer system 100 can estimate the weight of each variable based on the wellness to correlate observed data. The computer system 100 can plot the observed and modeled data for each variable, and, based on the plot, estimate the capability of the variable to describe a statistical fit of the data by coefficient of determination. For example, the computer system 100 can assign a weight value of 22 to landfills, 83 to accident hazard liquid, 48 to coalmines, 40 to incident gas distribution and 20 to incident gas transmission.

Figure 3:
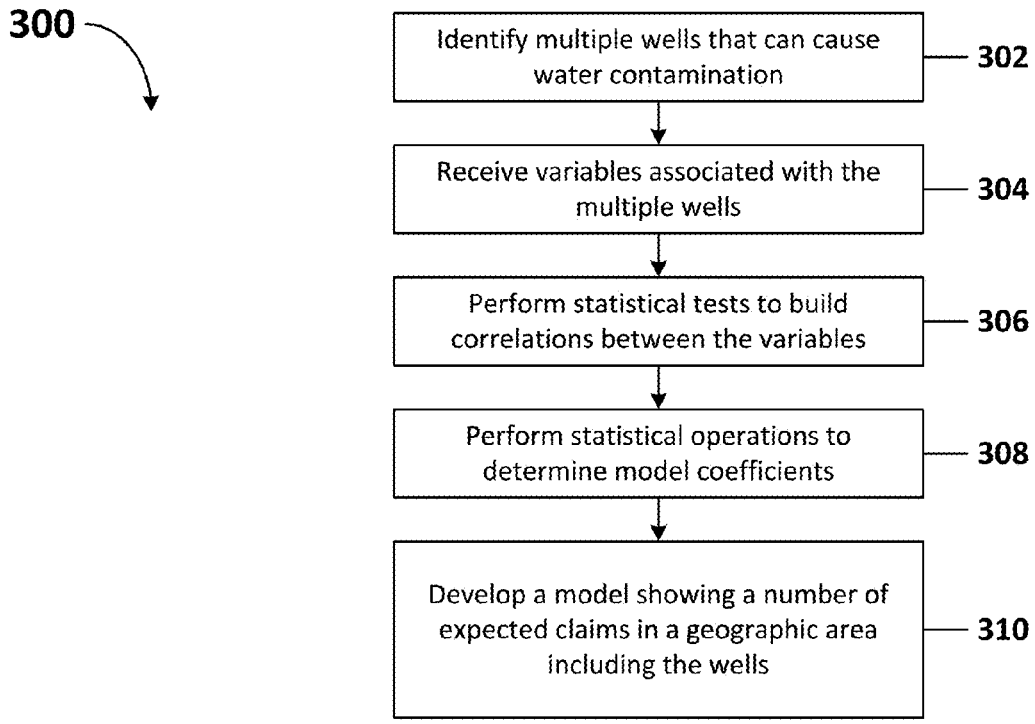
FIG. 3 is a flowchart of an example of a process to develop a mathematical model to determine a number of effective claims of water contamination in a geographic area from wells.

Another source of water contamination in a geographic area includes wells, e.g., active wells, plugged wells, injection wells, orphaned wells, or other types of wells. FIG. 3 is a flowchart of an example of a process 300 to develop a mathematical model to determine a number of effective claims of water contamination in a geographic area from wells. Anthropogenic sources are sources of environmental contamination originating in human activity in the geographic area. The process 300 can be implemented as computer instructions stored on the computer-readable medium 102 and executed by the data processing apparatus 104.

Figure 6F:
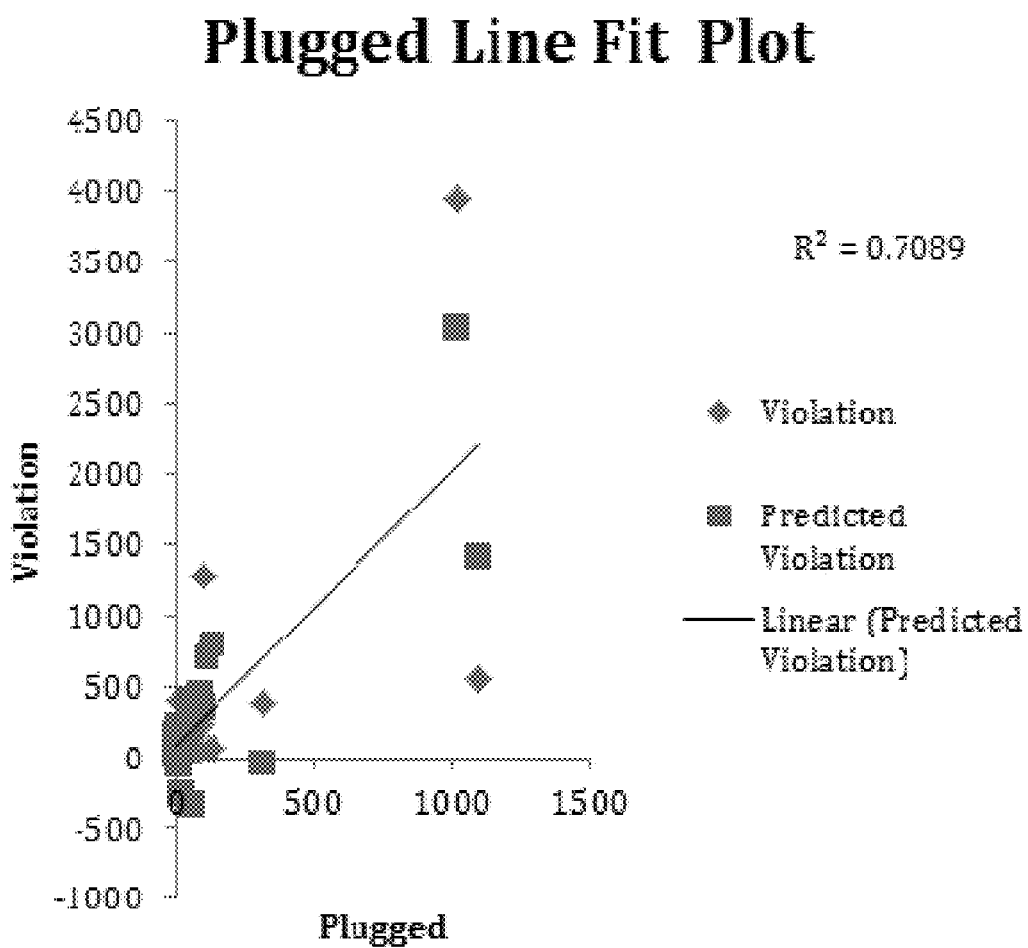
Figure 6G:
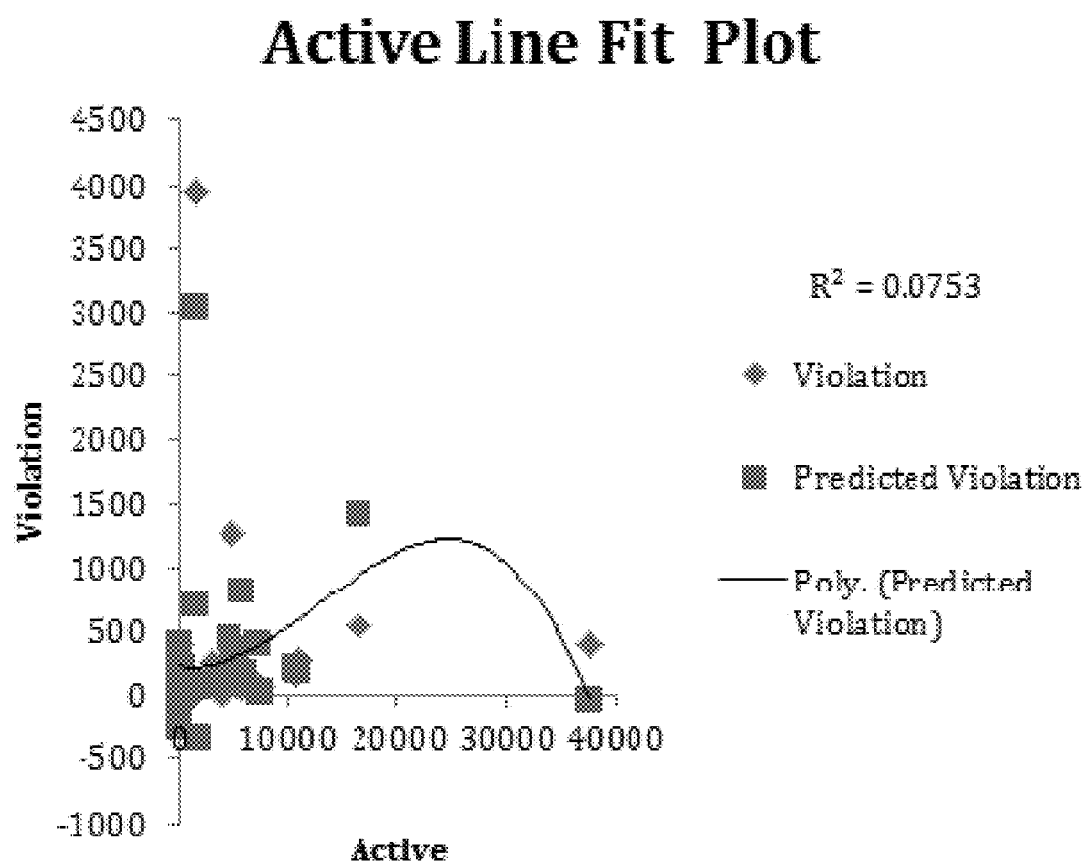
Figure 6H:
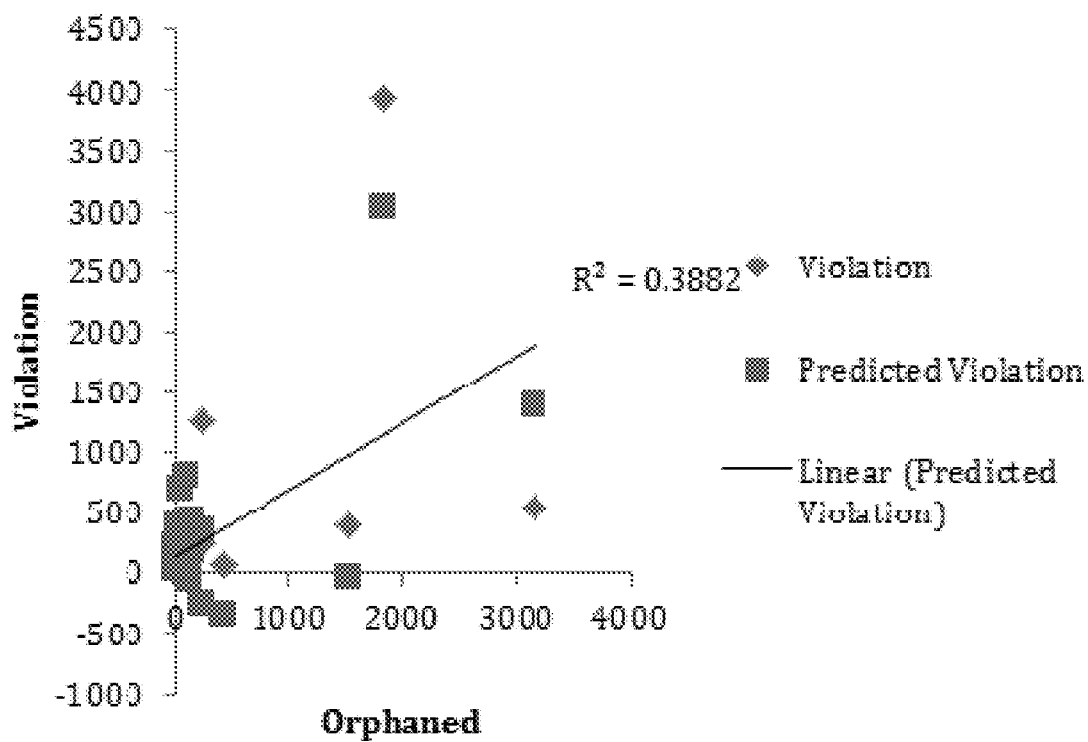

At 302, multiple wells that can cause water contamination in a geographic area can be determined. In some implementations, the wells can be correlated to identify a subset of the identified wells that are related. At 304, variables associated with the multiple wells can be identified. At 306, statistical tests can be performed to build correlations between the variables associated with the wells in the subset. FIG. 6F is a plot showing a line fit plot implemented for plugged wells. FIG. 6G is a plot showing an output (e.g., a Line Fit plot) of a linearity test implemented by the computer system 100 for active wells. FIG. 6H is a plot showing an output of a linearity test implemented by the computer system 100 for orphaned wells. Each of the wells represented in FIGS. 6F-6H are included in the geographic area.

At 308, statistical operations can be performed to determine model coefficients. At 310, a mathematical model showing a number of expected claims in a geographic area including the subset of wells can be developed. In some implementations, the computer system 100 can implement some or more of the operations in process 300 in a manner similar to those described above with reference to FIG. 2 and anthropogenic sources.

An example of regression statistics generated by the computer system for wells is shown below. As described below, results showed that 70% of the data point fit the statistical developed model. In other words, the observed data have 70% capability to predict future outcome.

TABLE 14

| Regression Statistics | |
|---|---|
| Multiple R | 0.838524 |
| R Square | 0.703123 |
| Adjusted R Square | 0.674393 |
| Standard Error | 387.08 |
| Observations | 35 |

The computer system 100 can also conduct analysis of variance to analyze the differences between group means and their associated procedures among and between groups.

TABLE 15

ANOVA analysis.
ANOVA

|  | df | SS | MS | F | Significance F |
|---|---|---|---|---|---|
| Regression | 3 | 11000617 | 3666872 | 24.4734 | 2.58E−08 |
| Residual | 31 | 4644759 | 149830.9 | | |
| Total | 34 | 15645376 | | | |

Results showed very low p-value and as a result statistical significance between and among groups. The computer system 100 can be implemented to develop a relationship between effective claims and different well types based on a multi-variables correlation analysis. The orphaned and plugged wells had high significance p-value and active wells came in the second order at 95% significance level as the table below shows.

TABLE 16

ANOVA table.

|  | Coefficients | Standard Error | t Stat | P-value | Lower 95% | Upper 95% | Lower 90.0% | Upper 90.0% |
|---|---|---|---|---|---|---|---|---|
| Intercept | 43.73193 | 81.6919 | 0.535328 | 0.596243 | −122.88 | 210.3437 | −94.7782 | 182.2421 |
| Plugged | 6.110722 | 1.018676 | 5.998692 | 1.23E−06 | 4.033119 | 8.188325 | 4.383538 | 7.837906 |
| Active | 0.017911 | 0.014287 | 1.253637 | 0.219346 | −0.01123 | 0.04705 | −0.00631 | 0.042135 |
| Orphaned | −1.78455 | 0.442128 | −4.03627 | 0.00033 | −2.68627 | −0.88282 | −2.53418 | −1.03491 |

The model developed by the computer system 100 for wells can be represented by Equation 2.

$$Y = 43.7 + 6.11P + 0.018A - 1.78O \quad \text{(Equation 2)}$$

In Equation 2, Y represents the number of potential complaints of water contamination, and P, A, and O represent a number of plugged wells, a number of active wells, and a number of orphaned wells, respectively. The computer system 100 can estimate a weight of each well type based on the wellness to correlate observed with modeled data. For example, the computer system 100 can estimate a weight value of 7 for active wells, 38 for orphaned wells, and 70 for plugged wells.

In some situations, the computer system 100 can determine that the geographic area includes both anthropogenic sources and wells. In such implementations, the computer system 100 can determine the number of potential complaints of water contamination (i.e., the effective claims) by adding the number of potential complaints determined using Equation 1 and that determined using Equation 2.

Figure 4:
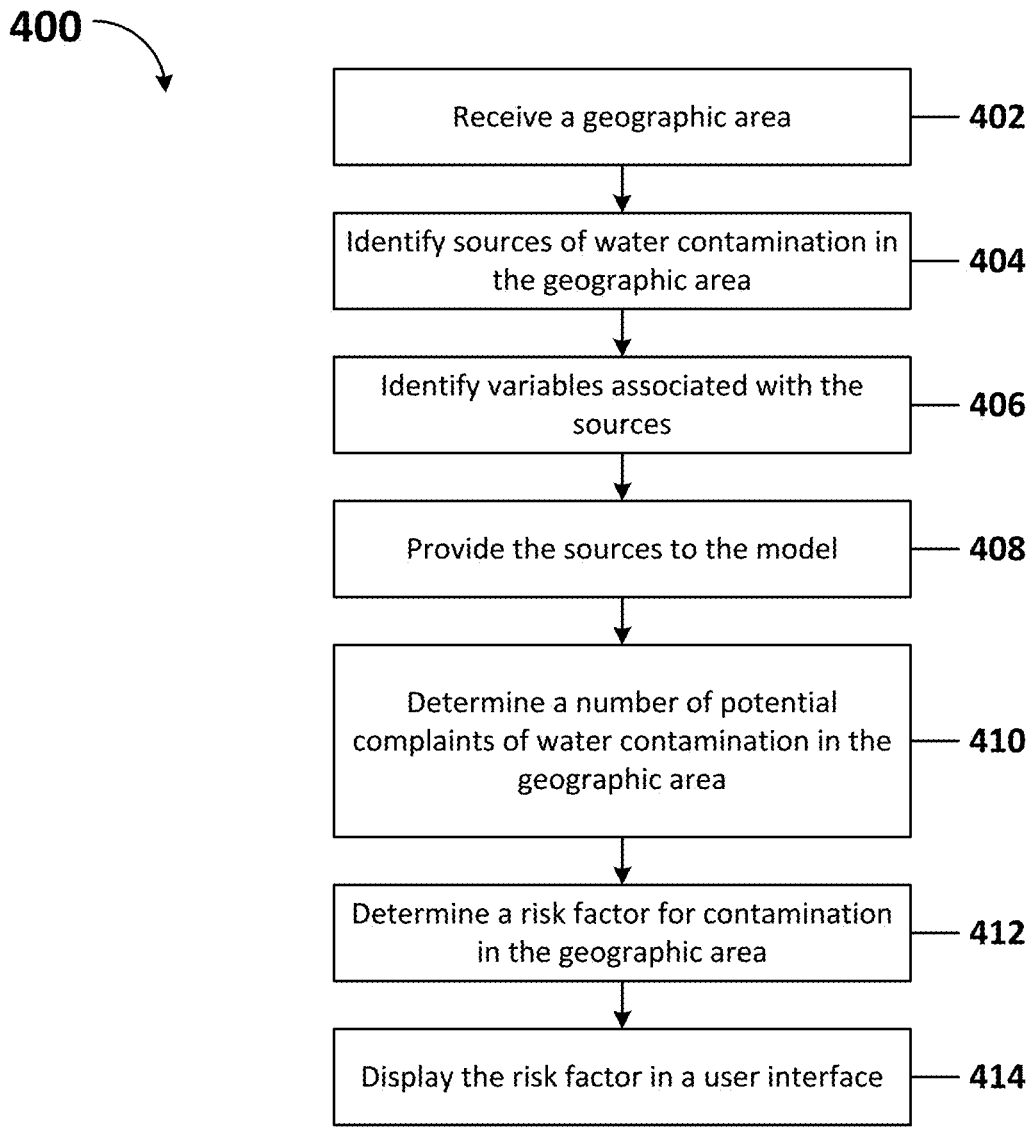
FIG. 4 is a flowchart of an example of a process to determine risk of water contamination based on a number of effective claims.

FIG. 4 is a flowchart of an example of a process 400 to determine risk of water contamination based on a number of effective claims. In some implementations, the computer system 100 can implement the process 400. At 402, a geographic area is received. For example, a user of the computer system 100 provides identifiers identifying the geographic area. At 404, sources of water contamination in the geographic area are identified. For example, the computer system 100 identifies the sources of water contamination, including one or more of anthropogenic sources or wells. As described above, the multiple sources can be filtered and a subset of the multiple sources selected based, in part, on factors including correlations between the sources, established causality between the sources and water contamination, and other factors. Consequently, some sources (e.g., landfill, coal mine, orphaned wells) can be disregarded from the analysis for a first geographic area. For a second, different geographic area, same or different sources, relative to the first geographic area, can be disregarded when determining the subset of sources.

At 408, the sources are provided to the model. For example, the computer system 100 provides a number of each source included in the subset to the model developed for the geographic area by implementing processes, such as those described above with reference to FIGS. 2 and 3, for the geographic area identified at 402. At 410, a number of potential complaints of water contamination in the geographic area is determined. For example, the computer system 100 determines effective claims arising from anthropogenic sources and effective claims arising from wells in the geographic area identified at 402. The computer system 100 determines a sum of the effective claims as the number of potential complaints of water contamination in the geographic area.

At 412, a risk factor for contamination in the geographic area is determined. The risk factor represents a risk of water contamination in the geographic area based, in part, on the number of potential complaints, i.e., the effective claims. In some implementations, the computer system 100 can determine the risk factor by applying an Inverse Distance Weighting (IDW) model. The model includes a deterministic approach for multi-variate interpolation with known scattered set points. The computer system 100 can assign a threshold value for each category. For example, the computer system 100 can determine that the number of potential complaints is greater than a first threshold number of potential complaints. In response, the computer system 100 can determine that the geographic area has a high risk factor for water contamination. Alternatively or in addition, the computer system 100 can determine that the number of potential complaints is less than or equal to the first threshold and greater than a second threshold number of potential complaints, the second threshold being less than the first threshold. In response, the computer system 100 can determine that the geographic area has a medium risk factor for water contamination. Alternatively or in addition, the computer system 100 can determine that the number of potential complaints is less than or equal to the second threshold. In response, the computer system 100 can determine that the geographic area has a low risk factor for water contamination. For example, the first threshold can be 110 and the second threshold can be 55. Based on these thresholds, the computer system 100 can design effective claims intervals as shown below in Table 17.

TABLE 17

Effective Claims intervals.

| Risk Rating | EC Interval |
|---|---|
| Low | <55 |
| Medium | 55-110 |
| High | >110 |

At 414, the risk factor is displayed in a user interface. For example, the computer system 100 can generate a user interface 116 for display in the display device 106. The user interface 116 can include an image 118 of the geographic area that the computer system 100 has analyzed. In the image 118, the computer system 100 can identify a low risk area 120, a medium risk area 122 and a high risk area 126 by implementing the techniques to determine the risk factor as described above. Some geographic areas may have only one risk rating (i.e., high risk, medium risk, or low risk), while other geographic areas may have more than one risk. Consequently, the computer system 100 can identify one or more areas of risk in the image 118 of the geographic area. In some implementations, the computer system 100 can display different areas of risk in different color, e.g., red for high risk area, yellow for medium risk area, green for low risk area. Alternatively or in addition, the computer system 100 can display the different areas of risk using other visual techniques that facilitate easy discerning of the different risk areas. In some implementations, the computer system 100 can display image objects (e.g., image object 128a, image object 128b, image object 128c, or other image objects), each of which represents a source of water contamination included in the subset for the geographic area. The computer system 100 can show a legend 130, e.g., a scale, using which the user can identify different areas of risk in the image 118 of the geographic area.

The techniques described above can be implemented to develop a mathematical model to determine effective claims for a geographic area from the lowest level of granularity (e.g., a municipality in a county) to the largest level of granularity (e.g., an entire country). An example for developing a mathematical model for the state of Texas is described below with reference to plots shown in FIGS. 7A-7D.

For example, a user of the computer system 100 identified Texas as the geographic area in which the risk of water contamination is to be determined. In some situations, the user identified a location in Texas in which a fracture treatment is being considered and requested an output indicating the risk of water contamination due to the proposed fracture treatment. In response, the computer system 100 identified multiple sources of water contamination, including anthropogenic sources and wells, in Texas. The sources included coal mines, incidents of gas distribution, incidents of hazard liquid, injection wells, landfills, orphaned wells, plugged wells, and active wells.

The computer system 100 implemented a correlation analysis of the various sources to ensure developing representative models. A result of the correlation analysis is shown in Table 18.

distribution did not show any correlation with the effective claims. Consequently, the computer system 100 filtered these sources and included the remaining sources in the subset of the multiple sources.

The computer system 100 then applied statistical analysis between the correlated variables using multiregression analysis after reviewing the tests' pre-requirements. A summary of the statistical analysis implemented by the computer system 100 is shown in Table 19.

TABLE 19

| Regression Statistics SUMMARY OUTPUT | |
|---|---|
| Multiple R | 0.538077 |
| R Square | 0.389527 |
| Adjusted R Square | 0.266328 |
| Standard Error | 11.48568 |
| Observations | 254 |

TABLE 18

Result of correlation analysis.

| | Claim | Coal mines | Gas Distribution | Hazard Liquid | Injection Wells | Landfills | Orphaned | Plugged | Active Wells |
|---|---|---|---|---|---|---|---|---|---|
| Claim | 1 | | | | | | | | |
| Coal mines | −0.023231942 | 1 | | | | | | | |
| Gas Distribution | 0.028786536 | 0.708860102 | 1 | | | | | | |
| Hazard Liquid | 0.113934181 | 0.382904497 | 0.559765 | 1 | | | | | |
| Injection Wells | 0.276137197 | −0.041629573 | −0.01324 | 0.156202 | 1 | | | | |
| Landfills | −0.05621039 | 0.066782114 | 0.114383 | −0.02081 | −0.03693 | 1 | | | |
| Orphaned | 0.319667458 | 0.001737859 | 0.025692 | 0.074086 | 0.529426 | 0.10634 | 1 | | |
| Plugged | 0.528463493 | 0.040576908 | 0.104191 | 0.225317 | 0.527742 | 0.06478 | 0.615126 | 1 | |
| Active Wells | 0.40033459 | 0.041929989 | 0.03595 | 0.172837 | 0.692602 | 0.038647 | 0.695541 | 0.756508 | 1 |

From the result of the correlation analysis, the computer system 100 determined that coal mines, landfills and gas The computer system 100 further performed ANOVA tests, the results of which are shown in Table 20.

TABLE 20

ANOVA test results.
ANOVA

| | df | SS | MS | F | Significance F |
|---|---|---|---|---|---|
| Regression | 8 | 13171.07 | 1646.383 | 12.48009 | 5.4087E−15 |
| Residual | 245 | 32320.59 | 131.9208 | | |
| Total | 253 | 45491.65 | | | |

| | Coefficients | Standard Error | t Stat | P-value | Lower 95% |
|---|---|---|---|---|---|
| Intercept | 1.63409 | 0.96848 | 1.687273 | 0.092824 | −0.2735194 |
| Coalmines | −1.0553 | 1.432901 | −0.73648 | 0.462144 | −3.877677 |

TABLE 20-continued

ANOVA test results.
ANOVA

| | | | | | |
|---|---|---|---|---|---|
| Gas_Distribution | 0.540227 | 2.145583 | 0.251786 | 0.801418 | −3.685915 |
| Hazard_Liquid | 0.006413 | 0.195069 | 0.032876 | 0.973801 | −0.3778137 |
| Injection_Wells | −0.00051 | 0.001655 | −0.31048 | 0.756461 | −0.0037744 |
| Landfills | −0.57515 | 0.348134 | −1.65209 | 0.099797 | −1.2608677 |
| Orphaned | 0.000837 | 0.040965 | 0.020421 | 0.983724 | −0.0798526 |
| Plugged | 0.005245 | 0.000843 | 6.223917 | 2.09E−09 | 0.00358518 |
| Active_Wells | 9.46E−05 | 0.000547 | 0.173012 | 0.862784 | −0.000982 |

From the ANOVA test results, the computer system 100 determined that the p-value was significant at 95% confidence interval. The computer system 100 then developed models for all correlated variables and used the developed models to predict the effective claim in the state of Texas. For orphaned wells, the computer system 100 determined a model represented by Equation 3:

$$Y=(0.1688 \cdot X)+3.6057 \quad \text{(Equation 3)}$$

Figure 7A:
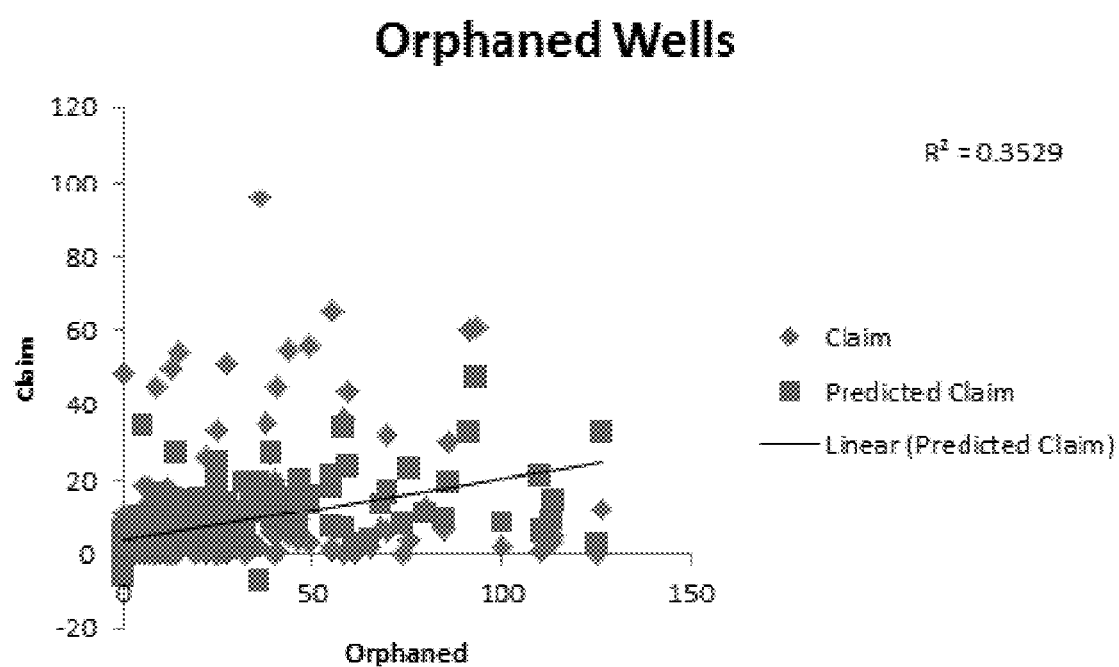
FIGS. 7A-7E are plots showing statistical tests performed for multiple sources of water contamination in Texas.

In Equation 3, Y represents the predicted effective claim and X represents the total number of orphaned wells. FIG. 7A is a plot comparing the claims and predicted claims determined using Equation 3.

For injection wells, the computer system 100 determined a model represented by Equation 5:

$$Y=(0.006 \cdot X)+5.4098 \quad \text{(Equation 4)}$$

Figure 7B:
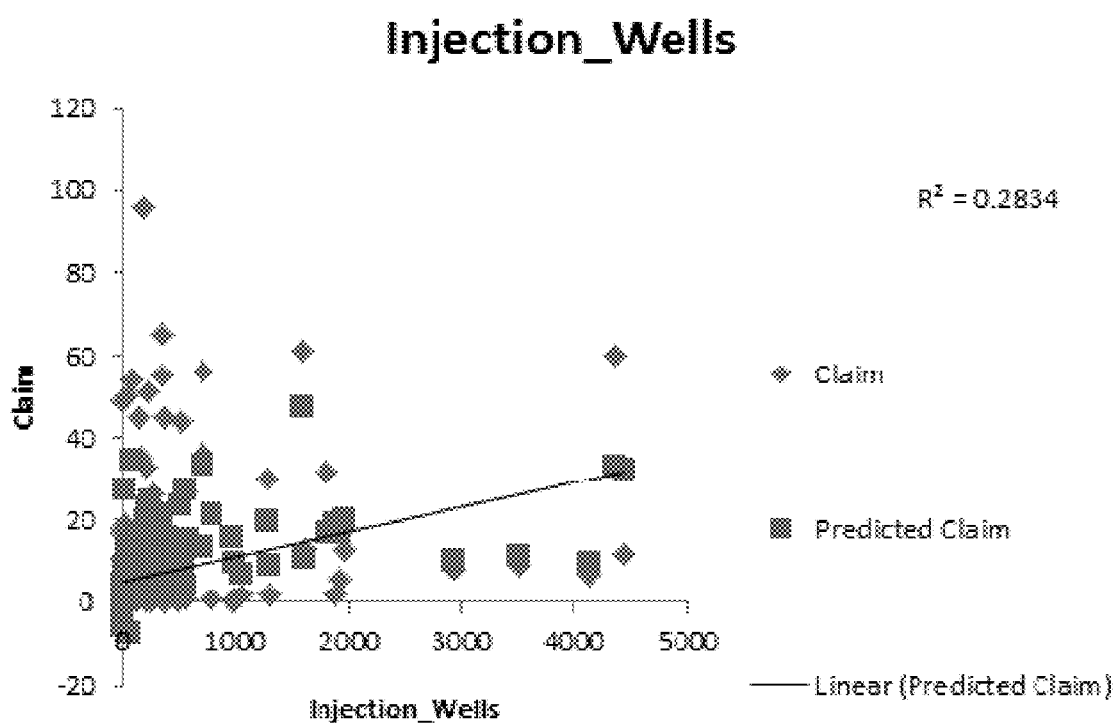

In Equation 4, Y represents the predicted effective claim and X represents the total number of injection wells. FIG. 7B is a plot comparing the claims and predicted claims determined using Equation 4.

For active wells, the computer system 100 determined a model represented by Equation 3:

$$Y=(0.0021 \cdot X)+2.8559 \quad \text{(Equation 5)}$$

Figure 7C:
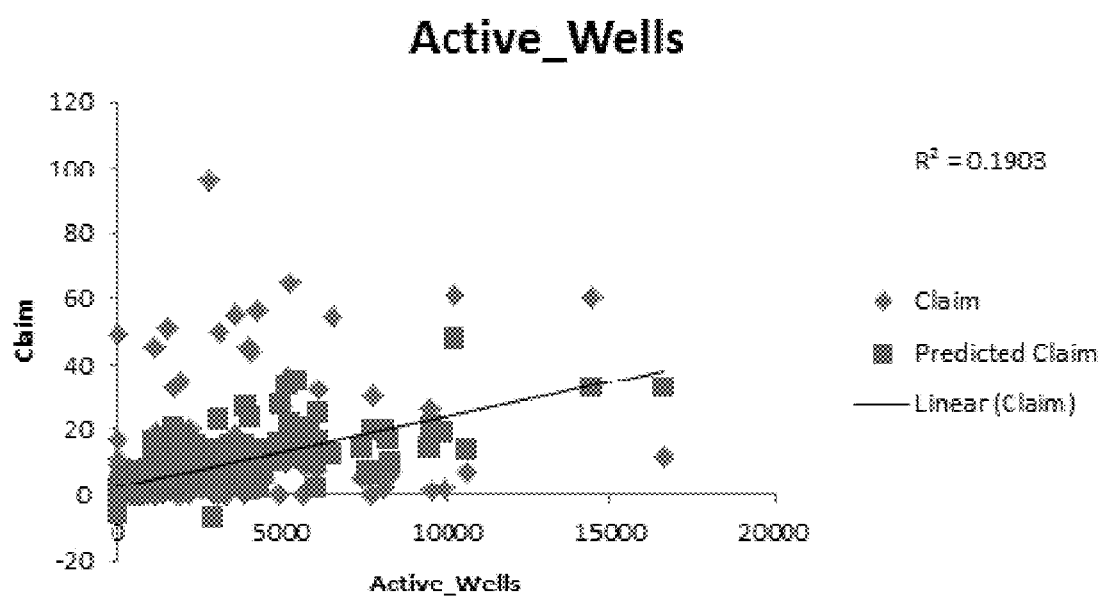

In Equation 5, Y represents the predicted effective claim and X represents the total number of injection wells. FIG. 7C is a plot comparing the claims and predicted claims determined using Equation 5.

For plugged wells, the computer system 100 determined a model represented by Equation 6:

$$Y=(0.0052 \cdot X)+1.428 \quad \text{(Equation 6)}$$

Figure 7D:
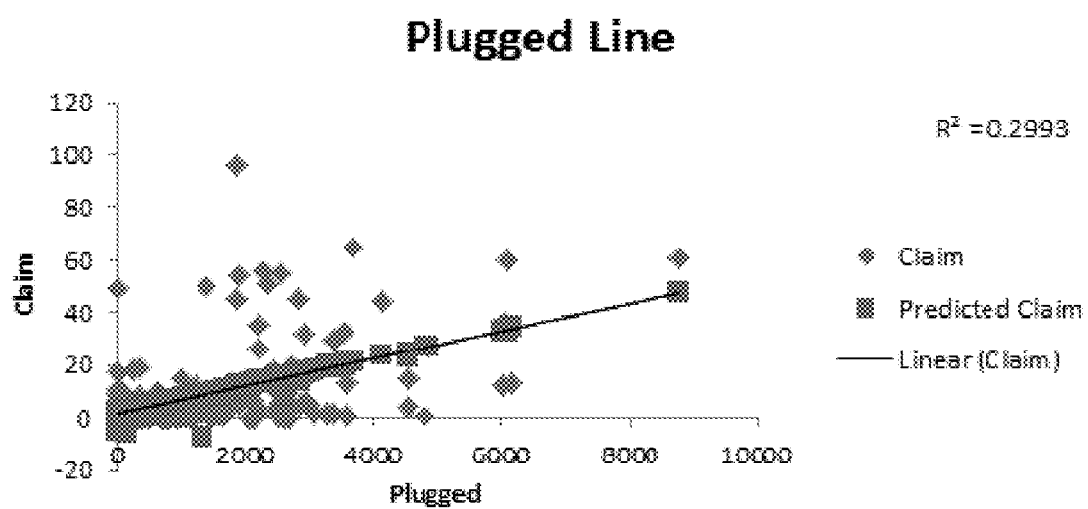

In Equation 6, Y represents the predicted effective claim and X represents the total number of plugged wells. FIG. 7D is a plot comparing the claims and predicted claims determined using Equation 6.

For incidents of hazard liquid wells, the computer system 100 determined a model represented by Equation 7:

$$Y=(0.3293 \cdot X)+6.4593 \quad \text{(Equation 7)}$$

Figure 7E:
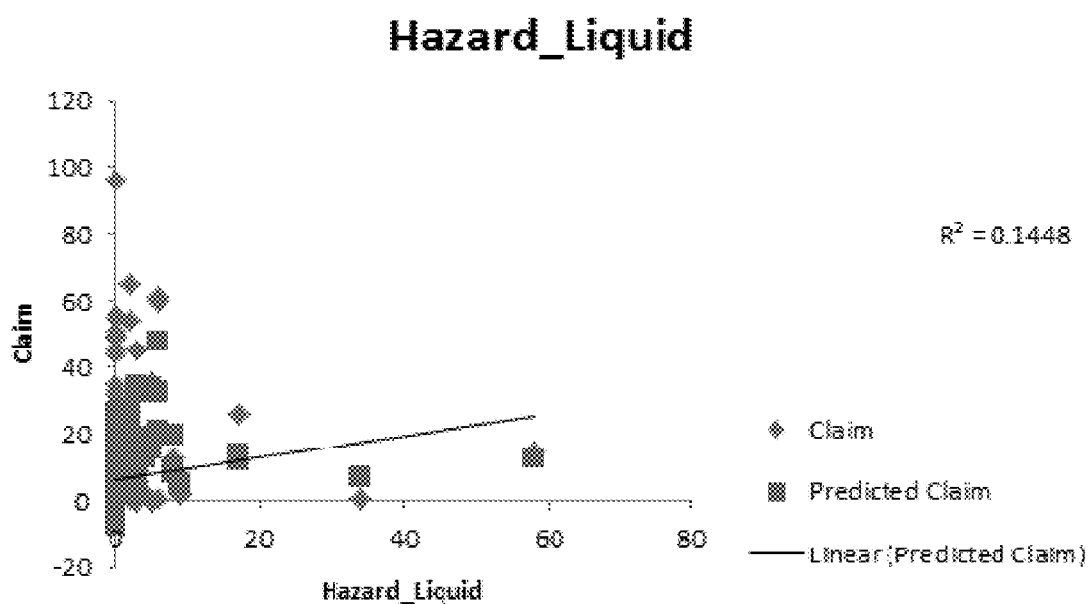

In Equation 7, Y represents the predicted effective claim and X represents the total number of incidents of hazard liquid. FIG. 7E is a plot comparing the claims and predicted claims determined using Equation 7.

For each variable in Equations 3-7, the computer system determined weights as shown in Table 21.

TABLE 21

Weights for variables.

| NO. | Variable | Weight |
|---|---|---|
| 1 | Orphaned well | 35 |
| 2 | Injection well | 28 |
| 3 | Active well | 19 |
| 4 | Plugged well | 30 |
| 5 | Hazard Liquid | 15 |

The results demonstrate that similar techniques can be implemented for any geographic area (e.g., any country, any state in the country, any granular division of the state, etc.) for which information about the sources of water contamination is available.

In some implementations, the computer system 100 can determine a distance between any two set points (e.g., a reference location and a source of water contamination) in a format of latitude and longitude coordinates by implementing the equations described below. The equations described below account for the Earth being spheroid rather than flat, and consequently enhance distance calculation by 0.5% relative to equations that treat the Earth as flat.

For the coordinates: (nLat1,nLon1),(nLat2,nLon2) in degrees, and the 'Earth's radius in Kilometers (nRadius=6371)

nDLat=deg2rad(nLat2− nLat1)
nDLon=deg2rad(nLon2− nLon1)
nLat1=deg2rad(nLat1)
nLat2=deg2rad(nLat2)
nA=(Sin(nDLat/2)*Sin(nDLat/2))+Cos(nLat1)*Cos(nLat2)*(Sin(nDLon/2)*Sin(nDLon/2))
nC=2*Atn2(Sqr(nA), Sqr(1−nA))
nD=nRadius*nC 'in km
d=nD/1.609344 'in mile
function deg2rad makes conversion from degrees to radians
function sin is the sine function that take angle in radian.
function cos is the cosine function that take angle in radian.
function sqr is the square root (power 0.5)
function Atn2(a,b) is the arctangent in radian.
function a cos is the arc cosine function in radian.
Equations used for distance dnew "New Equation":
theta=nLon1− nLon2
dist=Sin(deg2rad(nLat1))*Sin(deg2rad(nLat2))+Cos(deg2rad(nLat1))*Cos(deg2rad(nLat2))*Cos(deg2rad(theta))
dist=a cos(dist)
dist=rad2deg(dist)
dnew=dist*60*1.1515

Implementations of the subject matter and the operations described in this disclosure can be implemented in digital electronic circuitry, or in computer software, firmware, or hardware, including the structures disclosed in this disclosure and their structural equivalents, or in combinations of one or more of them. Implementations of the subject matter described in this disclosure can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, for example, a machine-generated electrical, optical, or electromagnetic signal that is generated to encode information for transmission to suitable receiver apparatus for execution by a data processing apparatus. A computer storage medium, for example, the computer-readable medium, can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical and/or non-transitory components or media (for example, multiple CDs, disks, or other storage devices).

In some implementations, the operations described in this disclosure can be implemented as a hosted service provided on a server in a cloud computing network. For example, the computer-readable storage media can be logically grouped and accessible within a cloud computing network. Servers within the cloud computing network can include a cloud computing platform for providing cloud-based services. The terms "cloud," "cloud computing," and "cloud-based" may be used interchangeably as appropriate without departing from the scope of this disclosure. Cloud-based services can be hosted services that are provided by servers and delivered across a network to a client platform to enhance, supplement, or replace applications executed locally on a client computer. The system can use cloud-based services to quickly receive software upgrades, applications, and other resources that would otherwise require a lengthy period of time before the resources can be delivered to the system.

The operations described in this disclosure can be implemented as operations performed by a data processing apparatus on data stored on one or more computer-readable storage devices or received from other sources. The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, for example, an FPGA (field programmable gate array) or an ASIC (application-specific integrated circuit). The apparatus can also include, in addition to hardware, code that creates an execution environment for the computer program in question, for example, code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (for example, one or more scripts stored in a markup language document), in a single file dedicated to the program in question, or in multiple coordinated files (for example, files that store one or more modules, sub-programs, or portions of code). A computer program can be deployed to be executed on one computer or on multiple computers that are located at one site or distributed across multiple sites and interconnected by a communication network.

The processes and logic flows described in this disclosure can be performed by one or more programmable processors executing one or more computer programs to perform actions by operating on input data and generating output. The processes and logic flows can also be performed by, and apparatus can also be implemented as, special purpose logic circuitry, for example, an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a Global Positioning System (GPS) receiver, or a portable storage device (for example, a universal serial bus (USB) flash drive), to name just a few. Devices suitable for storing computer program instructions and data include all forms of non-volatile memory, media and memory devices, including by way of example semiconductor memory devices, for example, EPROM, EEPROM, and flash memory devices; magnetic disks, for example, internal hard disks or removable disks; magneto-optical disks; and CD-ROM and DVD-ROM disks. The processor and the memory can be supplemented by, or incorporated in, special purpose logic circuitry.

To provide for interaction with a user, implementations of the subject matter described in this disclosure can be implemented on a computer having a display device, for example, a CRT (cathode ray tube) or LCD (liquid crystal display) monitor, for displaying information to the user, and a keyboard, a pointing device, for example, a mouse or a trackball, or a microphone and speaker (or combinations of them) by which the user can provide input to the computer. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Implementations of the subject matter described in this disclosure can be implemented in a computing system that includes a back-end component, for example, as a data server, or that includes a middleware component, for example, an application server, or that includes a front-end component, for example, a client computer having a graphical user interface or a Web browser through which a user can interact with an implementation of the subject matter described in this disclosure, or any combination of one or more such back-end, middleware, or front-end components. The components of the system can be interconnected by any form or medium of digital data communication, for example, a communication network. Examples of communication networks include a local area network ("LAN") and a wide area network ("WAN"), an inter-network (for example, the Internet), and peer-to-peer networks (for example, ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (for example, an HTML page) to a client device (for example, for purposes of displaying data to and receiving user input from a user interacting with the client device). Data generated at the client device (for example, a result of the user interaction) can be received from the client device at the server.

While this disclosure contains many specific implementation details, these should not be construed as limitations on the scope of any implementations or of what may be claimed, but rather as descriptions of features specific to particular implementations of particular implementations. Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

The invention claimed is:

1. A computer-implemented method to determine a risk of water contamination, the method comprising:
receiving, by a computer system, identification of a geographic area in which a risk of water contamination is to be determined;
in response to receiving the identification of the geographic area:
identifying, by the computer system, a plurality of sources of water contamination located in the geographic area, wherein the plurality of sources of water contaminations include a plurality of anthropogenic sources including at least one or more of a landfill, a coal mine, a reported accident hazard liquid, a reported incident gas distribution, or incident gas transmission gathering;
determining, by the computer system, a risk factor representing a risk of water contamination in the geographic area by applying a number of each source of water contamination to a model to determine a risk of water contamination in the geographic area, wherein the model is based, in part, on the number of each source of water contamination in the plurality of sources;
providing, by the computer system, the risk factor as the risk of water contamination in the geographic area; and
classifying, by the computer system, the geographic area as having at least one of a high risk, a medium risk, or a low risk of water contamination based on a result of comparing the number of potential complaints to the threshold number of potential complaints.

2. The computer-implemented method of claim 1, wherein each source of water contamination has a greater likelihood of causing water contamination in the geographic area compared to sources not included in the plurality of sources.

3. The computer-implemented of claim 2, wherein identifying the plurality of sources comprises:
performing a correlation analysis on the plurality of sources located in the geographic area; and
identifying correlated sources in response to performing the correlation analysis.

4. The computer-implemented method of claim 1, wherein determining the risk factor comprises:
identifying a plurality of variables associated with the subset of the plurality of sources, the plurality of variables including the number of each source of water contamination included in the subset; and
determining a number of potential complaints of water contamination in the geographic area by applying the number of each source of water contamination to the model.

5. The computer-implemented of claim 4, wherein identifying the plurality of variables includes:
accessing a plurality of databases that store information associated with the plurality of sources located in the geographic area, the information including the plurality of variables; and
retrieving the plurality of variables from one or more of the plurality of databases.

6. The computer-implemented of claim 4, wherein determining the risk factor comprises comparing the number of potential complaints to a threshold number of potential complaints; and
classifying the geographic area as having at least one of a high risk, a medium risk, or a low risk of water contamination comprises classifying the geographic area based on a result of comparing the number of potential complaints to the threshold number of potential complaints.

7. The computer-implemented of claim 4, further comprising developing the model to determine a number of potential complaints of water contamination in the geographic area by:
performing statistical operations on the plurality of variables to determine the number of potential complaints; and
determining a coefficient for each source of water contamination based, in part, on results of the statistical operations.

8. The computer-implemented of claim 4, wherein the model is represented by $Y=3.21-(0.04 \cdot A)+(0.79 \cdot B)+(0.16 \cdot C)+(0.15 \cdot D)+(0.01 \cdot E)$, wherein Y represents the number of potential complaints of water contamination, and A, B, C, D and E represent a number of landfills, a number of coal mines, a number of reported accident hazard liquid, a number of incident gas distribution, and a number of incident gas transmission gathering, respectively.

9. The computer-implemented of claim 1, wherein the plurality of sources of water contaminations include a plurality of wells including at least one or more of plugged wells, active wells, injection wells, or orphaned wells.

10. The computer-implemented of claim 9, wherein the model is represented by $Y=43.7+(6.11 \cdot P)+(0.018 \cdot A)-(1.78 \cdot O)$, wherein Y represents the number of potential complaints of water contamination, and P, A, and O represent a number of plugged wells, a number of active wells, and a number of orphaned wells, respectively.

11. A non-transitory computer-readable medium storing instructions executable by a computer system to determine a risk of water contamination, the instructions executable to perform operations comprising:
receiving, by a computer system, identification of a geographic area in which a risk of water contamination is to be determined;
in response to receiving the identification of the geographic area:
identifying, by the computer system, a plurality of sources of water contamination located in the geographic area, wherein the plurality of sources of water contaminations include a plurality of anthropogenic sources including at least one or more of a landfill, a coal mine, a reported accident hazard liquid, a reported incident gas distribution, or incident gas transmission gathering;
determining, by the computer system, a risk factor representing a risk of water contamination in the geographic area by applying a number of each source of water contamination to a model to determine a risk of water contamination in the geographic area, wherein the model is based, in part, on the number of each source of water contamination in the plurality of sources;
providing, by the computer system, the risk factor as the risk of water contamination in the geographic area; and
classifying, by the computer system, the geographic area as having at least one of a high risk, a medium risk, or a low risk of water contamination based on a result of comparing the number of potential complaints to the threshold number of potential complaints.

12. The non-transitory computer-readable medium of claim 11, wherein determining the risk factor comprises:
identifying a plurality of variables associated with the subset of the plurality of sources, the plurality of variables including the number of each source of water contamination included in the subset; and
determining a number of potential complaints of water contamination in the geographic area by applying the number of each source of water contamination to the model.

13. The non-transitory computer-readable medium of claim 12, wherein identifying the plurality of sources comprises:
performing a correlation analysis on the plurality of sources located in the geographic area; and
identifying correlated sources in response to performing the correlation analysis.

14. The non-transitory computer-readable medium of claim 11, wherein identifying the plurality of variables includes:
accessing a plurality of databases that store information associated with the plurality of sources located in the geographic area, the information including the plurality of variables; and
retrieving the plurality of variables from one or more of the plurality of databases.

15. The non-transitory computer-readable medium of claim 14, wherein determining the risk factor comprises comparing the number of potential complaints to a threshold number of potential complaints; and
classifying the geographic area as having at least one of a high risk, a medium risk, or a low risk of water contamination comprises classifying the geographic area based on a result of comparing the number of potential complaints to the threshold number of potential complaints.

16. The non-transitory computer-readable medium of claim 14, wherein the operations further comprise developing the model to determine a number of potential complaints of water contamination in the geographic area by:
performing statistical operations on the plurality of variables to determine the number of potential complaints; and
determining a coefficient for each source of water contamination based, in part, on results of the statistical operations.

17. The non-transitory computer-readable medium of claim 11, wherein the plurality of sources of water contaminations include a plurality of anthropogenic sources including at least one or more of a landfill, a coal mine, a reported accident hazard liquid, a reported incident gas distribution, or incident gas transmission gathering, and wherein the model is represented by $Y=3.21-(0.04 \cdot A)+(0.79 \cdot B)+(0.16 \cdot C)+(0.15 \cdot D)+(0.01 \cdot E)$, wherein Y represents the number of potential complaints of water contamination, and A, B, C, D and E represent a number of landfills, a number of coal mines, a number of reported accident hazard liquid, a number of incident gas distribution, and a number of incident gas transmission gathering, respectively.

18. The non-transitory computer-readable medium of claim 11, wherein the plurality of sources of water contaminations include a plurality of wells including at least one or more of plugged wells, active wells, injection wells, or orphaned wells, wherein the model is represented by $Y=43.7+(6.11 \cdot P)+(0.018 \cdot A)(1.78 \cdot O)$, wherein Y represents the number of potential complaints of water contamination, and P, A, and O represent a number of plugged wells, a number of active wells, and a number of orphaned wells, respectively.

19. A system comprising:
data processing apparatus; and
a computer-readable medium storing instructions executable by the data processing apparatus to determine a risk of water contamination, the instructions executable to perform operations comprising:

receiving, by the data processing apparatus, identification of a geographic area in which a risk of water contamination is to be determined;

in response to receiving the identification of the geographic area:

identifying, by the data processing apparatus, a plurality of sources of water contamination located in the geographic area, wherein the plurality of sources of water contaminations include a plurality of anthropogenic sources including at least one or more of a landfill, a coal mine, a reported accident hazard liquid, a reported incident gas distribution, or incident gas transmission gathering;

determining, by the data processing apparatus, a risk factor representing a risk of water contamination in the geographic area by applying a number of each source of water contamination to a model to determine a risk of water contamination in the geographic area, wherein the model is based, in part, on the number of each source of water contamination in the plurality of sources;

providing, by the data processing apparatus, the risk factor as the risk of water contamination in the geographic area; and classifying, by the data processing apparatus, the geographic area as having at least one of a high risk, a medium risk, or a low risk of water contamination based on a result of comparing the number of potential complaints to the threshold number of potential complaints.

* * * * *